US012591937B1

(12) United States Patent
Berg

(10) Patent No.: US 12,591,937 B1
(45) Date of Patent: *Mar. 31, 2026

(54) INTEGRATED DATA AND PREDICTIVE OUTPUTS FOR SMALL BUSINESS HEALTHCARE SOLUTIONS

(71) Applicant: Redirect Health, Inc., Scottsdale, AZ (US)

(72) Inventor: David F. Berg, Phoenix, AZ (US)

(73) Assignee: Redirect Health, Inc., Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/228,175

(22) Filed: Jun. 4, 2025

Related U.S. Application Data

(63) Continuation of application No. 18/585,917, filed on Feb. 23, 2024, now Pat. No. 12,333,610, which is a continuation-in-part of application No. 18/495,968, filed on Oct. 27, 2023, said application No. 18/585,917 is a continuation-in-part of application No. 18/495,978, filed on Oct. 27, 2023.

(60) Provisional application No. 63/421,364, filed on Nov. 1, 2022, provisional application No. 63/421,935, filed on Nov. 2, 2022, provisional application No. 63/448,551, filed on Feb. 27, 2023, provisional application No. 63/448,522, filed on Feb. 27, 2023.

(51) Int. Cl.
| | |
|---|---|
| *G06Q 40/00* | (2023.01) |
| *G06Q 40/08* | (2012.01) |
| *G16H 20/00* | (2018.01) |

(52) U.S. Cl.
CPC ............. *G06Q 40/08* (2013.01); *G16H 20/00* (2018.01)

(58) Field of Classification Search
CPC ............................... G06Q 40/08; G16H 20/00
See application file for complete search history.

(56) References Cited

U.S. PATENT DOCUMENTS

| | | |
|---|---|---|
| 7,653,558 B2 | 1/2010 | Schoenberg |
| 8,321,239 B2 | 11/2012 | Hasan et al. |
| 8,583,570 B2 | 11/2013 | Hartley et al. |
| | (Continued) | |

OTHER PUBLICATIONS

Beyond a Technical Perspective: Understanding Big Data Capabilities in Health Care; 2015 48th Hawaii International Conference on System Sciences (2015, pp. 3044-3053); Yichuan Wang, Leeann Kung, Chaochi Ting, Terry Anthony Byrd; Jan. 5, 2015.. (Year: 2015).*

(Continued)

*Primary Examiner* — Tien C Nguyen
(74) *Attorney, Agent, or Firm* — CALDWELL LLC

(57) ABSTRACT

The present invention is directed to systems for data integration and analysis using artificial intelligence networks to generate predictive outputs based on one or more inputs. The present invention incorporates healthcare data from a variety of sources and databases into a single system for predictive analysis using artificial intelligence. The present invention incorporates multifaceted authorization to access data from a variety of databases and integrate the data into a single data warehouse. The system of the present invention is further configured to analyze the integrated data to identify predictors, and subsequently uses the predictors to determine a predictive output based on an input.

20 Claims, 14 Drawing Sheets

(56)                    References Cited

U.S. PATENT DOCUMENTS

| | | | |
|---|---|---|---|
| 8,924,238 | B1 | 12/2014 | Nidy et al. |
| 8,930,225 | B2 | 1/2015 | Morris |
| 9,495,700 | B2 | 11/2016 | Hoch et al. |
| 10,423,759 | B1 | 9/2019 | Harris, Sr. et al. |
| 10,628,138 | B2* | 4/2020 | Pandit .................... G06N 20/00 |
| 10,943,407 | B1* | 3/2021 | Morgan ................. G16H 15/00 |
| 10,971,255 | B2* | 4/2021 | Krishnan ............... G16H 50/30 |
| 11,030,666 | B2 | 6/2021 | Ketchel, III et al. |
| 11,081,217 | B2* | 8/2021 | Zarkoob ................. G16H 50/20 |
| 11,101,043 | B2* | 8/2021 | Krishnan ............. G06N 3/0442 |
| 11,217,331 | B2 | 1/2022 | Vishnubhatla et al. |
| 11,443,384 | B2 | 9/2022 | Brisimi et al. |
| 11,449,913 | B2 | 9/2022 | Ketchel, III |
| 11,501,381 | B2 | 11/2022 | Hur et al. |
| 11,538,112 | B1 | 12/2022 | Singh et al. |
| 11,721,429 | B1 | 8/2023 | Mayer et al. |
| 11,900,464 | B1 | 2/2024 | Flynn |
| 2003/0181832 | A1* | 9/2003 | Carnahan ............. A61B 5/4528 |
| | | | 600/595 |
| 2005/0075912 | A1 | 4/2005 | Bealke et al. |
| 2006/0023244 | A1* | 2/2006 | Mitsui ................... G06F 3/1205 |
| | | | 358/1.13 |
| 2007/0239484 | A1 | 10/2007 | Arond et al. |
| 2008/0154649 | A1 | 6/2008 | Babyak et al. |
| 2009/0187429 | A1 | 7/2009 | Scalet et al. |
| 2010/0063830 | A1 | 3/2010 | Kenedy et al. |
| 2012/0123891 | A1 | 5/2012 | Patel |
| 2012/0278100 | A1 | 11/2012 | Macoviak |
| 2014/0324472 | A1 | 10/2014 | Delaney et al. |
| 2014/0343959 | A1 | 11/2014 | Hasegawa et al. |
| 2015/0088541 | A1 | 3/2015 | Yao |
| 2015/0134353 | A1 | 5/2015 | Ferrell et al. |
| 2015/0339602 | A1 | 11/2015 | Schlosser et al. |
| 2016/0171180 | A1 | 6/2016 | Yagnyamurthy et al. |
| 2016/0225096 | A1 | 8/2016 | Wells et al. |
| 2016/0379243 | A1* | 12/2016 | Kalish ................ G06Q 30/0242 |
| | | | 705/14.41 |
| 2017/0140109 | A1* | 5/2017 | Kheifetz ............... G16H 50/50 |
| 2017/0161433 | A1 | 6/2017 | Perretta |
| 2017/0188894 | A1* | 7/2017 | Chang .................. A61B 5/1121 |
| 2017/0308979 | A1 | 10/2017 | Frankel et al. |
| 2017/0357844 | A1* | 12/2017 | Comaniciu ........... G16H 30/00 |
| 2018/0052968 | A1 | 2/2018 | Hickle et al. |
| 2018/0211727 | A1* | 7/2018 | Zarkoob ................ G16H 10/60 |
| 2019/0041835 | A1* | 2/2019 | Cella ...................... G06N 3/006 |
| 2019/0088356 | A1* | 3/2019 | Oliver ................... G16H 50/20 |
| 2019/0206524 | A1* | 7/2019 | Baldwin ............... G06F 40/169 |
| 2019/0214143 | A1 | 7/2019 | Cha |
| 2019/0251694 | A1* | 8/2019 | Han ......................... G06N 3/08 |
| 2019/0333155 | A1* | 10/2019 | Natesan Ramamurthy ................. |
| | | | G06N 20/00 |
| 2019/0378619 | A1* | 12/2019 | Meyer ...................... G06N 3/08 |
| 2020/0020427 | A1 | 1/2020 | Yarbray et al. |
| 2020/0035341 | A1 | 1/2020 | Kain et al. |
| 2020/0074573 | A1 | 3/2020 | Op Den et al. |
| 2020/0134691 | A1 | 4/2020 | Wiseman, Sr. |
| 2021/0248268 | A1* | 8/2021 | Ardhanari .............. G06N 20/00 |
| 2021/0272067 | A1 | 9/2021 | Santos et al. |
| 2021/0350910 | A1 | 11/2021 | Dastmalchi et al. |
| 2021/0383927 | A1 | 12/2021 | Godden et al. |
| 2022/0115135 | A1 | 4/2022 | Lieberman |
| 2022/0207241 | A1 | 6/2022 | Bettencourt-Silva et al. |
| 2022/0293272 | A1* | 9/2022 | Pang ...................... G16H 20/00 |
| 2022/0301072 | A1 | 9/2022 | Wang et al. |
| 2022/0309592 | A1 | 9/2022 | Zahora et al. |
| 2022/0359067 | A1 | 11/2022 | Mccallum et al. |
| 2022/0359080 | A1 | 11/2022 | Basu |
| 2022/0383276 | A1 | 12/2022 | Hummer |
| 2022/0398490 | A1* | 12/2022 | Han ....................... G06N 20/00 |
| 2023/0076559 | A1 | 3/2023 | Sankarapu et al. |
| 2023/0084146 | A1 | 3/2023 | Singh et al. |
| 2023/0170065 | A1* | 6/2023 | De Vries ................ G16H 50/30 |
| | | | 705/2 |
| 2023/0230681 | A1 | 7/2023 | Watters |
| 2023/0260048 | A1 | 8/2023 | Hayward et al. |
| 2023/0260610 | A1 | 8/2023 | Pelzer et al. |
| 2023/0298104 | A1 | 9/2023 | Diatto |
| 2023/0334590 | A1 | 10/2023 | Chehrazi et al. |
| 2024/0161932 | A1 | 5/2024 | Christine et al. |

OTHER PUBLICATIONS

A Comprehensive Review on Smart Decision Support Systems for Health Care; IEEE Systems Journal (vol. 13, Issue: 3, 2019, pp. 3536-3545); Mario W. L. Moreira, Joel J. P. C. Rodrigues, Valery Korotaev, Jalal Al-Muhtadi, Neeraj Kumar; Jan. 11, 2019. (Year: 2019).

Insight of big data analytics in healthcare industry; 2016 International Conference on Computing, Communication and Automation (ICCCA) (2016, pp. 95-100); Satwik Sabharwal, Samridhi Gupta, K. Thirunavukkarasu; Apr. 29, 2016. (Year: 2016).

Predictive analytics on Electronic Health Records (EH Rs) using Hadoop and Hive; 2015 IEEE International Conference on Electrical, Computer and Communication Technologies (ICECCT) (2015, pp. 1-5);Haritha Chennamsetty, Suresh Chalasani, Derek Riley; Mar. 1, 2015. (Year: 2015).

* cited by examiner

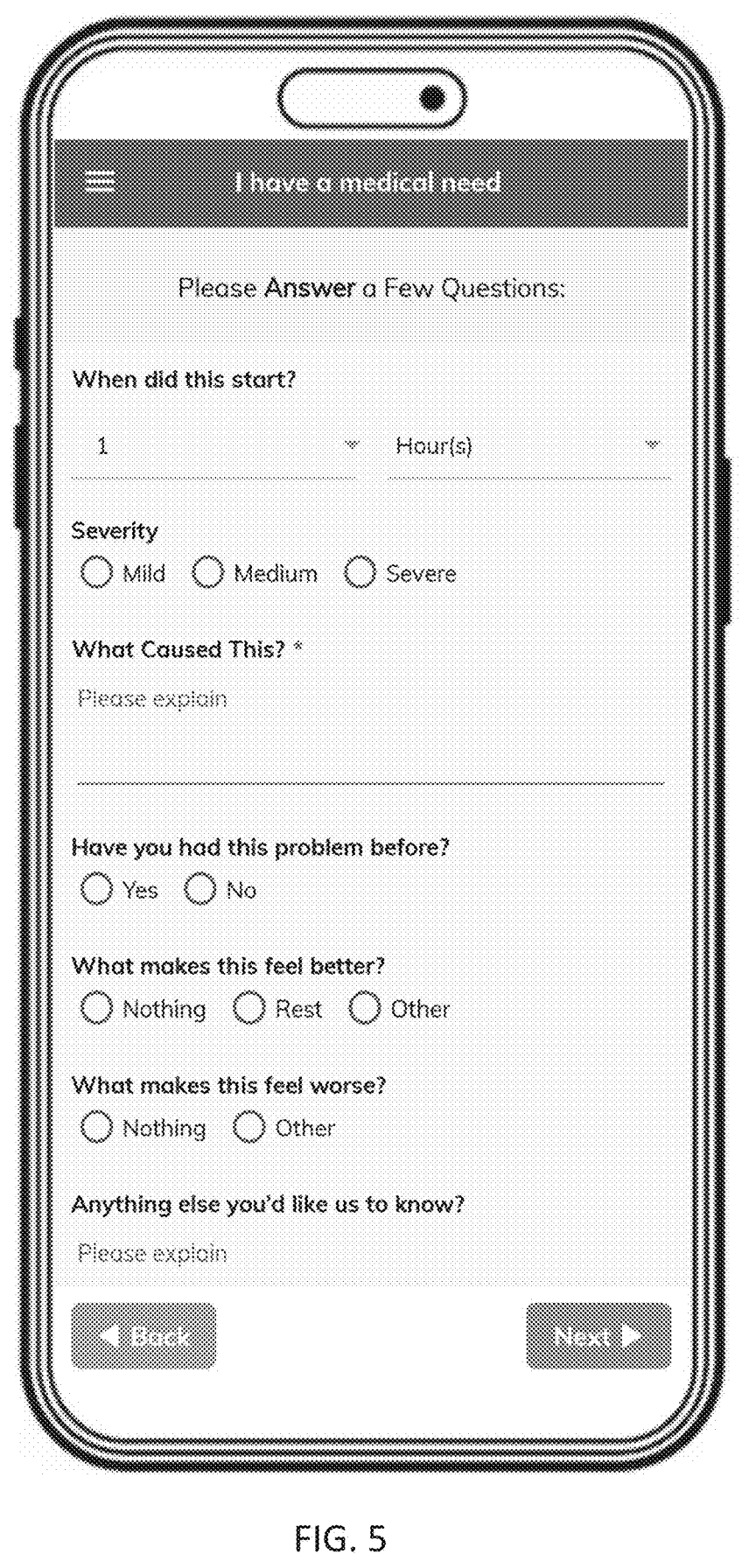

I have a medical need

Please Answer a Few Questions:

When did this start?

1      ▾     Hour(s)      ▾

Severity

○ Mild   ○ Medium   ○ Severe

What Caused This? *

Please explain

Have you had this problem before?

○ Yes   ○ No

What makes this feel better?

○ Nothing   ○ Rest   ○ Other

What makes this feel worse?

○ Nothing   ○ Other

Anything else you'd like us to know?

Please explain

◀ Back          Next ▶

FIG. 5

INTEGRATED DATA AND PREDICTIVE OUTPUTS FOR SMALL BUSINESS HEALTHCARE SOLUTIONS

CROSS REFERENCES TO RELATED APPLICATIONS

This application is a continuation of U.S. patent application Ser. No. 18/585,917, filed Feb. 23, 2024, which is a continuation-in-part of U.S. patent application Ser. No. 18/495,968, filed Oct. 27, 2023, which claims priority to and the benefit of U.S. Provisional Patent Application 63/421,364, filed Nov. 1, 2022, and U.S. patent application Ser. No. 18/495,978, filed Oct. 27, 2023, which claims priority to and the benefit of U.S. Provisional Patent Application No. 63/421,935, filed Nov. 2, 2022, each of which is incorporated herein by reference in its entirety. This application also claims priority to and the benefit of U.S. Provisional Patent Application No. 63/448,551, filed Feb. 27, 2023, and U.S. Provisional Patent Application No. 63/448,522, filed Feb. 27, 2023, each of which is incorporated herein by reference in its entirety.

BACKGROUND OF THE INVENTION

1. Field of the Invention

The present invention relates to systems for predictive healthcare solutions, and more specifically to data aggregation systems for accessing and analyzing health data to generate dynamic predictions for healthcare solutions.

2. Description of the Prior Art

It is generally known in the prior art to provide systems for collecting healthcare data.

Prior art patent documents include the following:

US Patent Pub. No. 2023/0334590 for Machine-Learning Driven Data Analysis Based on Demographics, Risk, and Need by inventors Chehrazi et al., filed Jun. 20, 2023 and published Oct. 19, 2023, is directed to a data processing system for recommending insurance plans implements obtaining an electronic copy of demographic information associated with a user; analyzing the demographic information with a first machine learning model to recommend a bundle of insurance policies based on the demographic information, wherein the first machine learning model is configured to group insured people having similar demographics into clusters and to generate the bundle of insurance policies based on predicted medical insurance consumption associated with a respective group into which the model predicts that the first user falls; customizing the recommended bundle of insurance policies based on the demographic information associated with the user to generate a customized bundle of insurance policies; generating an insurance recommendation report that presents the customized bundle of insurance policies to the user; and causing a user interface of a display of a computing device associated with the user to present the insurance recommendation report.

US Patent. Pub. No. 2020/0035341 for De-identification omic data aggregation platform with permitted third party access by inventors Kain et al., filed Apr. 8, 2019 and published Jan. 30, 2020, is directed to a system and method for the collection and aggregation of genomic, medical, and other data of interest for individuals and populations that may be of interest for analysis, research, pharmaceutical development, medical treatment, and so forth. Contributors become members of a community upon creation of an account and providing of data or files. The data is received and processed, such as to analyze, structure, perform quality control, and curate the data. Value or shares in one or more community databases are computed and attributed to each contributing member. The data is controlled to avoid identification or personalization. Third parties interested in the database information may contribute value (e.g., pay) for access and use. Value flows back to the members and to a system administrative entity.

US Patent Pub No. 2019/0214143 for System and method for creating and using a health risk profile of a patient by inventor Cha, filed Jan. 9, 2018 and published Jul. 11, 2019, is directed to a method of creating a local risk database for improving the speed of determining a health risk profile associated with a patient. The method may include retrieving patient medical information about a first patient. The method may also include performing a first data conversion procedure including: sending the patient medical information to a translation resource if there is no match between the patient medical information and the records in the database; receiving translated patient medical information from the translation resource; sending the translated patient medical information to a coding resource; and receiving, from the coding resource, a predetermined code associated with the translated medical information. Also, the method may include using the predetermined code to determine a patient health risk profile and adding to the database a record of an association between the predetermined code and the patient medical information.

U.S. Pat. No. 8,321,239 for System for communication of health care data by inventors Hasan et al., filed Nov. 30, 2011 and issued Nov. 27, 2012, is directed to a computer system that extracts health care data from one or more health care payors to identify meaningful relationships or patterns in treatments to compare the effectiveness of various treatment of specific diseases. This computer system includes a computer and a staging database. The computer is configured to communicate with one or more payor computer systems of a type that includes one or more databases storing records of the health care data from one or more payors over the Internet. The staging database is in communication with the computer and is configured to receive the health care data from each of the payor computer systems. The health care data from each of the payor computer systems is configured to be converted into a normalized format. The normalized data is the made available to determine comparative effectiveness of various treatments of specific diseases.

U.S. Pat. No. 7,653,558 for Consolidation of consumer interactions within a medical brokerage system by inventor Schoenberg, filed Apr. 7, 2008 and issued Jan. 6, 2010, is directed to agenda items which are generated based on a consumer's one or more interactions with a system. The agenda items are consolidated into an agenda, a graphical user interface is produced that when rendered on a display displays the agenda, and a request from the consumer to interact with one or more of the agenda items is received.

U.S. Pat. No. 11,501,381 for Method for learning and device for reviewing insurance review claim statement on basis of deep neural network by inventors Hur, et al., filed Aug. 7, 2020 and issued Nov. 15, 2022, is direct to a method for learning an insurance claim statement on a basis of a deep neural network, includes: receiving, by an insurance claim statement reviewing device, an input of a plurality of insurance review claim statements containing at least one of first information, second information, third information and fourth information; classifying, by the insurance claim statement reviewing device, the general items, the diagnosed patient injury/disease items, the treatment history items, or the prescription items; converting, by the insurance claim statement reviewing device, the categorical data or the numerical data; inputting, by the insurance claim statement reviewing device, the converted data; training, by the insurance claim statement reviewing device, the deep neural network using training data of the converted data; and verifying, by the insurance claim statement reviewing device, the deep neural network using verification data of the converted data.

US Patent Pub. No. 2023/0084146 for Machine learning systems and methods for processing data for healthcare applications by inventors Singh, et al., filed Nov. 22, 2022 and published Mar. 16, 2023, is directed to a method of predicting an outcome of a prior-authorization, claim, or appeal includes receiving, at a server, a natural language data file representing doctors notes from a provider visit related to a service instance; receiving, at the server, a structured data set including patient profile data, diagnosis and procedure codes, and quantitative data related to a payment requested; processing at least the natural language data file using a medical dictionary to output a set of key medical terms; processing, using a supervised machine learning algorithm, the structured data set and the set of key medical terms to predict an outcome of the payment requested; and outputting an indication of the predicted outcome of the payment requested.

US Patent Pub. No. 2023/0076559 for Explainable artificial intelligence based decisioning management system and method for processing financial transactions by inventors Sankarapu, et al., filed Nov. 15, 2021 and published Mar. 9, 2023, is directed to an explainable artificial intelligence based decisioning management method and system for processing financial transaction is disclosed. The method includes receiving a request for performing a financial transaction from applicant and from data sources. The method further includes performing a data sufficiency check using one or more neural network on the request by validating the request of the applicant with one or more external data sources. Further, the method includes generating a decision for the received request using neural network model if the data sufficiency check is successful. Additionally, the method includes validating the decision by reverse calculating, through the neural layers of the neural network model, an importance weightage distribution across each of the neural nodes. Also, the method includes generating a case assessment report for the generated decision based on the validation. Furthermore, the method includes performing the financial transaction with the applicant in response to the received request based on the generated case assessment report.

US Patent Pub. No. 2023/0260048 for Implementing Machine Learning For Life And Health Insurance Claims Handling by inventors Hayward, et al., filed Apr. 25, 2023 and published Aug. 17, 2023, is directed to techniques for implementing machine learning to improve claim handling are disclosed. In some scenarios, the machine-learning, analytics model may be trained in accordance with data that is relevant to insurance products, such as life and health insurance. A set of labeled historical claims each corresponding to a settlement amount may be analyzed to train an artificial neural network, A claim may be received from a user mobile device, and may be analyzed using the trained artificial neural network to predict a claim settlement, which may be used to generate a settlement offer. The settlement offer may be transmitted to the user's mobile device, and if a manifestation of acceptance is received from the user, then the claim may be automatically paid.

US Patent Pub. No. 2022/0115135 for Machine Learning Systems and Methods for Assessing Medical Interventions for Utilization Review by inventor Lieberman, filed Dec. 21, 2021 and published Apr. 14, 2022, is directed to systems and methods for determining the appropriateness of medical interventions. A machine learning system for determining the appropriateness of a selected medical intervention includes health-related data sources, the health-related data sources providing at least one data file of a first type, and a second data file of a second type. A machine learning module is configured to receive the first and second data files, perform a normalization procedure on at least one of the first and second data files, and apply at least one previously trained machine learning model to the normalized data files to produce a prediction output. The prediction output may include a confidence level associated with an appropriateness of the selected medical intervention.

US Patent Pub. No. 2022/0309592 for Systems and Methods for Prediction and Estimation of Medical Claims Payments by inventors Zahora, et al., filed Mar. 25, 2022 and published Sep. 29, 2022, is directed to systems and methods for calculating medical claims payment estimates may receive a medical claim for a first patient including billing code(s) and demographic data, apply the demographic data to identify payer(s) for the first patient, access a data universe including patient data collection(s) of patient data records for a second group of patients, payer data collection (s) of data records for payers, and a financial history data collection including financial data record(s) for the first patient, identify, for each billing code, a payer payment pattern based on a combination of the patient data records and payer data record(s) corresponding to the payer for the first patient, identify a patient payment pattern based on the financial data record(s), and apply the payer payment pattern and the patient payment pattern to the medical claim for the first patient to calculate a payment estimation for the medical claim.

U.S. Pat. No. 8,583,570 for Advanced data integrity by inventors Hartley, et al., filed Feb. 13, 2012 and issued Nov. 12, 2013, is directed to a payment integrity system that processes data, including data associated with a biometric technology. The system includes a discovery module to receive insurance records from a source of data, which includes the data associated with the biometric technology, the records providing information that pertain to at least one transaction. The discovery module includes a query component and an artificial intelligence engine to process the records to identify a second subset of the records having anomalous information, and provide a second analysis output indicative of the second subset. The system also includes an audit module to determine whether to instruct the artificial intelligence engine to analyze the records according to the outputs. The system facilitates resolution of a claim payment based on the first analysis output and the second analysis output.

US Patent Pub. No. 2023/0260610 for Value-based decision optimization module for healthcare by inventors Pelzer, et al., filed Apr. 24, 2023 and published Aug. 17, 2023, is directed to a method including retrieving an information for a subject, the information comprising a disease of the subject, a subject condition, and a previous condition. The method includes parsing a contract between a provider and a payor to identify a measurable value and identifying a contract success factor and a social determinant for the disease in the subject based on the subject condition, the measurable value, the previous condition, and the contract. The method also includes identifying multiple options available for the provider in a treatment of the disease in the subject. The method also includes identifying an expected condition based on the performance parameter and on the disease of the subject, and providing a recommendation to the provider fir an action to improve the expected condition. A system and a non-transitory, computer-readable medium storing instructions to perform the above method are also provided.

US Patent Pub. No. 2022/0301072 for Systems and methods for processing claims by inventors Wang, et al., filed Jun. 9, 2022 and published Sep. 22, 2022, is directed to Methods, systems, and apparatuses, including computer programs encoded on computer storage media, are provided for processing claims using both unstructured and structured policy documents, claim data, and customer and policy data, in conjunction with automatic requests for human intervention. Policy rules, benefit calculation formulae, necessary data points, and benefit requirements are extracted from policy documents using NLP and AI techniques. Unstructured claim data is converted to a structured form using natural language processing, information extraction, and AI techniques to identify and extract relevant information, including values for the data points and benefit conditions, then the combined structured data and converted unstructured data is processed to get all values for the data points and applicable benefit conditions. The relevant claim information is then further processed against the policy rules for eligibility assessment and benefit calculation formulae to generate a benefit payment amount and entitled additional benefits.

US Patent Pub. No. 2021/0272067 for Multi-Task Deep Learning of Employer-Provided Benefit Plans by inventors Santos, et al., filed Mar. 2, 2020 and published Sep. 2, 2021, is directed to a method for generating an employee benefit plan. The process collects employment data about employees of a plurality of business entities. The employment data comprises a number of dimensions of data collected from a number of sources. The process identifies a number of plan benefits for benefit plan for each of the business entities. The process determines metrics for the plan benefits during a given time interval. The process simultaneously models the plan benefits and the metrics for plan benefits to identify correlations among the dimensions of data and generalize rules for competitive benefit prediction. According to the modeling, the process predicts a number of competitive benefits for an employee benefit plan of a particular business entity based on the employment data of the particular business entity. The process generates the employee benefit plan for the particular business entity based on the number of competitive benefits.

US Patent Pub. No. 2022/0359080 for Multi-model member outreach system by inventor BASU, filed Jul. 11, 2022 and published Nov. 10, 2022, is directed to members outreach services to be offered to members of a health plan based on predictions generated by a prediction engine using data associated with the members. The prediction engine can include an ensemble of different base predictive models, and the prediction engine can use a weighted combination of base predictions produced by the different base predictive models to generate a final prediction associated with a member. A representative can attempt to contact the member based on an outreach ticket associated with the final prediction. The representative can also provide ticket feedback associated with the outreach, and the prediction engine can use the ticket feedback to adjust the weights associated with the different base predictive models.

U.S. Pat. No. 9,495,700 for Portfolio-level decision support by inventors Hoch, et al., filed Oct. 13, 2014 and issued Nov. 15, 2016, is directed to an invention that employs branded virtual characters to engage and educate users regarding an array of health-related insurance, financial, and other benefits, enabling informed decision-making during this complex process. Information is collected gradually on an "as-needed" basis to avoid overwhelming users with lengthy and redundant requests for information, while still providing a safe environment for users to freely discuss personal, health, financial and related sensitive issues. Throughout the process, the system employs a portfolio-driven approach to identify inter-dependencies among different benefit products and plans, and prioritize and recommend "portfolio-level" benefit solutions. Back-end components enable users to complete transactions (e.g., via third-party quoting and enrollment systems and employer HRIS systems, as well as via access to external medical and claims data), and provide third parties with access to the educational, decision-making and transactional aspects of this process, including various authoring and other tools to generate and modify system content over time.

U.S. Pat. No. 11,721,429 for Event prediction based on medical service and provider information using an artificial intelligence prediction engine by inventors Mayer, et al., filed Sep. 30, 2020 and issued Aug. 8, 2023, is directed to a method includes receiving information associated with a stimulus, the information associated with the stimulus comprising first information associated with a medical claim for services provided to a patient and second information associated with a provider that provided the services to the patient; and predicting, using an artificial intelligence engine, when an event will occur in response to the stimulus.

US Patent Pub. No. 2022/0359067 for Computer Search Engine Employing Artificial Intelligence, Machine Learning and Neural Networks for Optimal Healthcare Outcomes by inventors McCallum, et al., filed Jul. 14, 2022 and published Nov. 10, 2022, is directed to a machine learning system and method utilizing artificial intelligence that improves the provisioning of healthcare and reduces the total cost of healthcare and lost productivity. The approach creates a quantifiable assessment of quality and a ranking number measuring a provider's quality of healthcare services. The machine learning system makes a determination of quality based on a clinical evaluation database, an employee related time and attendance database, and a costing database. The system analyzes how quickly a provider returns an employee to work at or near pre-absence productivity and at what cost. The system creates a ranking number that provides employees with a comparison of providers. Employees may then be incentivized to seek high value providers.

US Patent Pub. No. 2020/0074573 for System and method for performing patient-specific cost-effectiveness analyses for medical interventions by inventors BUIJS, et al., filed Sep. 10, 2019 and published Mar. 5, 2020, is directed to a patient dataset including digital medical images and other patient data may be obtained. The other patient data may include specific patient health data associated with a patient and historical patient data derived from a population related to the patient. The historical patient data may indicate medical inventions provided to patients of the related population, health effects of the medical interventions, and costs of the medical interventions. In some embodiments, a neural network specific to the patient may be configured for a user application using at least part of the patient dataset. As an example, the user application may include neural network. Based on the specific patient health data, health effects and intervention costs related to individual interventions for the patient may be predict via the neural network of the user application. The net health benefits for the individual interventions may be provided via the user interface based on the predicted health effects and intervention costs.

US Patent Pub. No. 2022/0207241 for Analyzing and explaining a temporal evolution of policies and suggesting next steps by inventors Bettencourt-Silva, et al., filed Dec. 29, 2020 and published Jun. 30, 2020 is directed to a system and method for analyzing and explaining the temporal evolution of policies. The analysis of the temporal evolution of policies includes determining semantically related changes in the text of the corresponding policies over time and across the different versions of the (two or more) policy documents. An explanation of the temporal evolution of policies is provided consisting of human interpretable information relating each change to one or more events and/or contextual data. A next steps policy change is also suggested that includes a set of policy conditions based on potential future changes of similar policies and contextual data and event data. The suggestions are related to the policy relevant to the target cohort or individual. The system adapts machine learned models by receiving user feedback provided on an analysis of the correctness of the temporal evolution of policies, corresponding explanations and suggestions of the next actions.

US Patent Pub. No. 2015/0134353 for Health care services optimization platform, strategic purchasing & method related thereof by inventors Ferrell, et al., filed Nov. 12, 2014 and published May 14, 2015, is directed to a digital medical interface to help streamline the overall health care service provider experience by patients seeking care, negotiating costs associated with the care and paying for the services. The invention more specifically relates to a web-based/app-based software interface for a very unique combination of collection, display and use of medical treatment-related information using different remote devices and different databases of information. Further, the invention covers methods for reducing health care costs, including steering patients to appropriate low-cost alternatives and reducing the number of unnecessary procedures by providing patients with live guidance from a personal health care professional, implementing strategic buying procedures, reducing administrative overhead and making guaranteed payments to providers at the time of service, and guiding patients to appropriate preventive procedures based on factors such as their personal health risk assessment and prior claims history.

US Patent. Pub. No. 2014/0343959 for Analysis system and analysis method by inventors Hasegawa et al., filed May 16, 2014 and published Nov. 20, 2014, is directed to an analysis system comprising: an input unit to receive a medical cost of a insured person, intervention information on a provision of an intervention service and a start date of the intervention service; a propensity score calculation unit to analyze a relationship between the medical cost before the provision of the intervention service and the intervention information, and to calculate a propensity score of an intervention group and a propensity score of a nonintervention group; and an adjusted medical cost calculation unit to calculate adjusted medical costs of the intervention group before and after the provision of the intervention service by using the propensity score of the intervention group and medical costs of the intervention group before and after the provision of the intervention service, and to calculate adjusted medical costs of the nonintervention group before and after the provision of the intervention service.

U.S. Pat. No. 8,930,225 for Estimating healthcare outcomes for individuals by inventor Morris, filed Apr. 16, 2012 and issued Jan. 6, 2015, is directed to a method and apparatus for predicting a health benefit for an individual. Outcomes from a first simulation on a set of simulated individuals reflecting a population are stored and used to determine a first risk function and corresponding cost values. Outcomes from a second simulation on a set of simulated individuals reflecting having a healthcare intervention are stored and used to determine a second risk function reflecting the intervention and corresponding cost values of the intervention. A benefit function is derived from the difference of the first and second risk functions. A cost function that describes the cost of the intervention is derived from the respective cost values. The derived benefit function and cost function are used to predict the corresponding benefit and cost of the healthcare intervention for a given individual. Individuals can be ranked by degree of expected benefit.

US Patent Pub. No. 11,030,666 for Network-based marketplace service pricing tool for facilitating purchases of bundled services and products by inventors Ketchel et al., filed Nov. 15, 2019 and issued Jun. 8, 2021, is directed to an apparatus for pricing offers of healthcare services including an application server linked to a virtual payment system manager providing a pricing tool, a service pricing information database and a cost adjustment information database that are accessible by the application server. The pricing tool is operable to receive an indication of a healthcare service set that is respectively associated with a service detail information record included in the service pricing information database, dynamically calculating an adjusted physician fee for the primary service based on cost adjustment metrics for a geographic zone that corresponds to the specified location, and provide a recommended price for the indicated healthcare service set based on the calculated adjusted physician fee. A virtual money account database to maintain records of virtual funds of the user is provided and the virtual payment system manager is configured to allocate and distribute the virtual funds in the transaction marketplace system to virtual accounts of the user.

U.S. Pat. No. 11,449,913 for Prepaid bundled health, dental, and veterinary services with virtual payment distribution by inventor Ketchell, filed Dec. 6, 2021 and issued Sep. 20, 2022, is directed to apparatus and associated methods relate to presenting for selection services comprising at least one bundled set of healthcare services to be performed separately by respective providers, determining a bundle price for the at least one bundled set of healthcare services, and in response to receiving payment in an amount of the bundle price, generating a purchase data record selectively redeemable to receive each of the at least one bundled set of healthcare services, and assigning a unique confirmation number generated for the purchase data record. One or more service of the bundled set may be a dental or veterinary service. The bundle price may be based on a location or time at which at least one service will be performed and may be determined using a user's remaining insurance deductible. Payment may be disbursed to multiple providers of the bundled set of healthcare services. A payment may be virtual funds.

U.S. Pat. No. 11,443,384 for Intelligent policy covery [sic] gap discovery and policy coverage optimization by inventors Brisimi et al., filed Apr. 6, 2020 and issued Sep.

13, 2022, is directed to various embodiments for providing intelligent policy coverage optimization in a computing environment by a processor. One or more policy coverage gaps in one or more operational rules defined by one or more rules, policies, or a combination thereof and associated with one or more non-compliant policy claims associated with the one or more policy coverage gaps may be identified. The one or more policy coverage gaps may be ranked according to one or more selected criteria.

US Patent Pub. No. 2020/0020427 for Methods and systems for data analytics of metrics for outcomes and pay-for-performance models by inventors Yarbray et al., filed Jul. 11, 2019 and published Jan. 16, 2020, is directed to a computer-implemented method includes obtaining, by a processing device, patient notes from therapy sessions, each patient note includes an identity of a patient of a set of patients and an identity of a clinician of a set of clinicians. The method also includes detecting from the patient notes an outcome for each patient of the set of patients, resulting in a set of outcomes. The method also includes grouping, by the processing device, the set of patients based on the set of outcomes to create a group of favorable outcomes and a group of unfavorable outcomes, analyzing, by the processing device, at least one underlying cause in a difference between the group of favorable outcomes and the group of unfavorable outcomes to determine a root cause of favorable outcomes, and recommending a modification to future therapy sessions based on the root cause of favorable outcomes.

US Patent Pub. No. 2014/0324472 for Method and system for extraction and analysis of inpatient and outpatient encounters from one or more healthcare related information systems by inventors Delaney et al., filed Jul. 8, 2014 and published Oct. 30, 2014, is directed to systems and methods that facilitate extraction and analysis of patient encounters from one or more healthcare related information systems are provided. In an aspect, a system includes a reception component configured to receive information from a plurality of sources regarding courses of care of a plurality of patients, including information identifying activities associated with the courses of care, timing of the activities, resources associated with the activities, and caregiver personal associated with the activities. The system further includes an indexing component configured to generate an index that relates aspects of the information, a filter component configured to employ the index to identify a subset of the information related to a subset of the courses of care for patients associated with a similar medical condition, and an analysis component configured to compare aspects of the subset of the information to identify variance in the subset of the courses of care.

U.S. Pat. No. 11,217,331 for Pharmacy management and administration with bedside real-time medical event data collection by inventors Vishnubhatla et al., filed Nov. 18, 2016 and issued Jan. 4, 2022, is directed to methods and systems for automatically establishing an enhanced electronic health record (EHR) for a patient include an automatic data collection facility that collects data of a medically related event in proximity to a patient upon occurrence of the event. The collected data may include medication administration data such as medication, time of administration, administration of a dosage of medication, reaction data, and the like. The collected data is communicated to a real-time data integration facility that automatically integrates the data with a patient's electronic health record to establish an enhanced electronic health record.

US Patent Pub. No. 2018/0052968 for Computer assisted patient navigation and information systems and methods by inventors Hickle et al., filed Aug. 24, 2017 and published Jul. 16, 2019, is directed to a computer assisted patient navigational communication system for receiving electronic and oral communications from a patient, scanning data to determine the medical needs of the patient, and displaying relevant information to appropriate medical personnel who can immediately advise the patient of the most appropriate source of medical assistance relating to the patient's identified symptoms. Related methods are also described.

US Patent Pub. No. 2021/0350910 for System and method for supporting healthcare cost and quality management by inventors Dastmalchi et al., filed Mar. 12, 2021 and published Nov. 11, 2021, is directed to historical healthcare records are linked by patient and searched for instances of an episode of healthcare interaction, anchored by a predefined anchor event. Meaningful input and output variables applicable to the episode are identified. Machine learned models are developed which predict the effect that input process variables have on the output variables, and these models are written to a process change exploration data store. Then, through a GUI, a user interactively explores various schedules for changing physical healthcare processes, and the system visually forecasts resulting changes in total cost of an EHI, Planned process changes are implemented and the system visually tracks actual progress both of input process variable implementation and output variable changes. The user can use this information to modify implementation schedules for input process changes. The system can also predict total cost of a specific ongoing EHI long before actual financial claims data are available.

US Patent Pub. No. 2007/0239484 for System and method for managing patient bed assignments, bed occupancy, and staffing in a healthcare facility operation by inventors Arond et al., filed Mar. 16, 2007 and published Oct. 11, 2007, is directed to an integrated health care delivery network with enabling software and network technology to maximize bed resources, manage varying census levels, and avoid patient diversions through real-time monitoring, automation and communication, is disclosed. Preferably, the present invention is embodied in a Patient Agent Throughput Management System that interfaces with and complements the following existing healthcare facility systems: Admission/Discharge/Transfer (ADT); Scheduling System; Bed tracking (for housekeeping purposes); Security; Clinical Information Management; Human Resources; and Physician Information Management. The "Patient Agent" system is an easy-to-use business intelligence application that is designed to allow administrators, clinicians and managers to easily access, analyze and display real-time patient, staff and bed availability information from clinical and ancillary information systems. It enables users to see trends and relationships in hospital management data directly from their desktop personal computers.

US Patent Pub. No. 2012/0278100 for Remote, Adjunct, Credentialed Provider-Directed Healthcare Systems and Methods by inventor Macoviak, filed Apr. 28, 2011 and published Nov. 1, 2012, is directed to systems and methods for extending patient care effectiveness of a licensed primary healthcare provider facility, group, or individual and providing professional answering and triage services, comprising: a live, remote, adjunct healthcare provider, wherein said adjunct provider is credentialed by said licensed primary healthcare provider facility, group, or individual to provide remote adjunct care for one or more patients, wherein said adjunct provider is covered by medical malpractice insurance, wherein said patients are legally under the care of said licensed primary healthcare provider facility, group, or individual; a software module for providing said remote adjunct healthcare provider access to one or more electronic health records for said one or more patients; and a communications link between said remote adjunct healthcare provider and said patient or one or more onsite patient caregivers.

SUMMARY OF THE INVENTION

The present invention relates to systems for healthcare data aggregation and analysis, and more specifically to data aggregation systems for accessing and analyzing health data to generate dynamic predictions for healthcare solutions.

It is an object of this invention to provide a platform for data collection including the necessary licensure to obtain healthcare treatment information, health insurance information, personal device data, marketing and sales data, and data associated with a member account of a user interface of the platform.

In one embodiment, the present invention includes a system for dynamic healthcare navigation, including, a server computer including a data warehouse, a memory, and a processor, and at least one database including at least one secure data set, wherein the at least one database requires at least one authorization to access the at least one secure data set, wherein the server computer is configured to implement the at least one authorization to access the at least one secure data set, wherein the server computer is configured to access the at least one secure data set and store the at least one secure data set in the data warehouse, wherein the data warehouse implements a machine learning model (MLM), wherein the MLM is configured to analyze the at least one secure data set and tag predictors within the at least one secure data set, wherein the server computer is configured to receive a request associated with the predictors within the at least one secure data set, and wherein the server computer is configured to generate an output based on the predictors within the at least one secure data set.

In another embodiment, the present invention includes a system for dynamic healthcare navigation, including a server computer including a data warehouse, a memory, and a processor, a medical database including at least one secure medical data set, an insurance database including at least one secure insurance data set, and a third-party administrator (TPA) database including at least one secure TPA data set, wherein the medical database requires a medical authorization to access the at least one secure medical data set, wherein the insurance database requires an insurance authorization to access the at least one secure insurance data set, wherein the TPA database requires a TPA authorization to access the at least one secure TPA data set, wherein the server computer is configured to implement the medical authorization, the insurance authorization, and the TPA authorization to access the at least one secure medical data set, the at least one secure insurance data set, and the at least one secure TPA data set, wherein the server computer is configured to access the at least one secure medical data set, the at least one secure insurance data set, and the at least one secure TPA data set and store the at least one secure medical data set, the at least one secure insurance data set, and the at least one secure TPA data set in the data warehouse, wherein the data warehouse implements a machine learning model (MLM), wherein the MLM is configured to analyze the at least one secure medical data set, the at least one secure insurance data set, and the at least one secure TPA data set and tag predictors within the at least one secure medical data set, the at least one secure insurance data set, and the at least one secure TPA data set, wherein the server computer is configured to receive a request associated with the predictors within the at least one secure medical data set, the at least one secure insurance data set, and the at least one secure TPA data set, and wherein the server computer is configured to generate an output based on the predictors within the at least one secure medical data set, the at least one secure insurance data set, and the at least one secure TPA data set.

In yet another embodiment, the present invention includes a method for dynamic healthcare navigation, including implementing, via a server computer, at least one medical authorization, wherein the at least one medical authorization is granted by a medical license, accessing a secure medical database, wherein the at least one medical authorization is granted and the server computer is operable to access at least one secure medical data set stored on the secure medical database, storing the at least one secure medical data set on a data warehouse of the server computer, implementing, via the server computer, at least one insurance authorization, wherein the at least one insurance authorization is granted by an insurance license, accessing a secure insurance database, wherein the at least one insurance authorization is granted and the server computer is operable to access at least one secure insurance data set stored on the secure insurance database, storing the at least one secure insurance data set on a data warehouse of the server computer, analyzing the at least one secure medical data set and the at least one secure insurance data set, identifying at least one medical predictor within the at least one secure medical data set, wherein the at least one medical predictor is associated with a healthcare treatment plan, a price of a medical service or a medical good, or a successful medical treatment method, tagging the at least one medical predictor within the at least one secure medical data set, identifying at least one insurance predictor within the at least one secure insurance data set, wherein the at least one insurance predictor is associated with a claim payment, an insurance policy, or insurance sales data, tagging the at least one insurance predictor within the at least one secure medical data set, receiving, via a user device in network connection with the server computer, a request associated with the at least one medical predictor or the at least one insurance predictor, and generating an output based on at least one medical predictor or the at least one insurance predictor.

These and other aspects of the present invention will become apparent to those skilled in the art after a reading of the following description of the preferred embodiment when considered with the drawings, as they support the claimed invention.

BRIEF DESCRIPTION OF THE DRAWINGS

FIG. 5 is an exemplary GUI display of a platform of the present invention.

DETAILED DESCRIPTION

Figure 1:
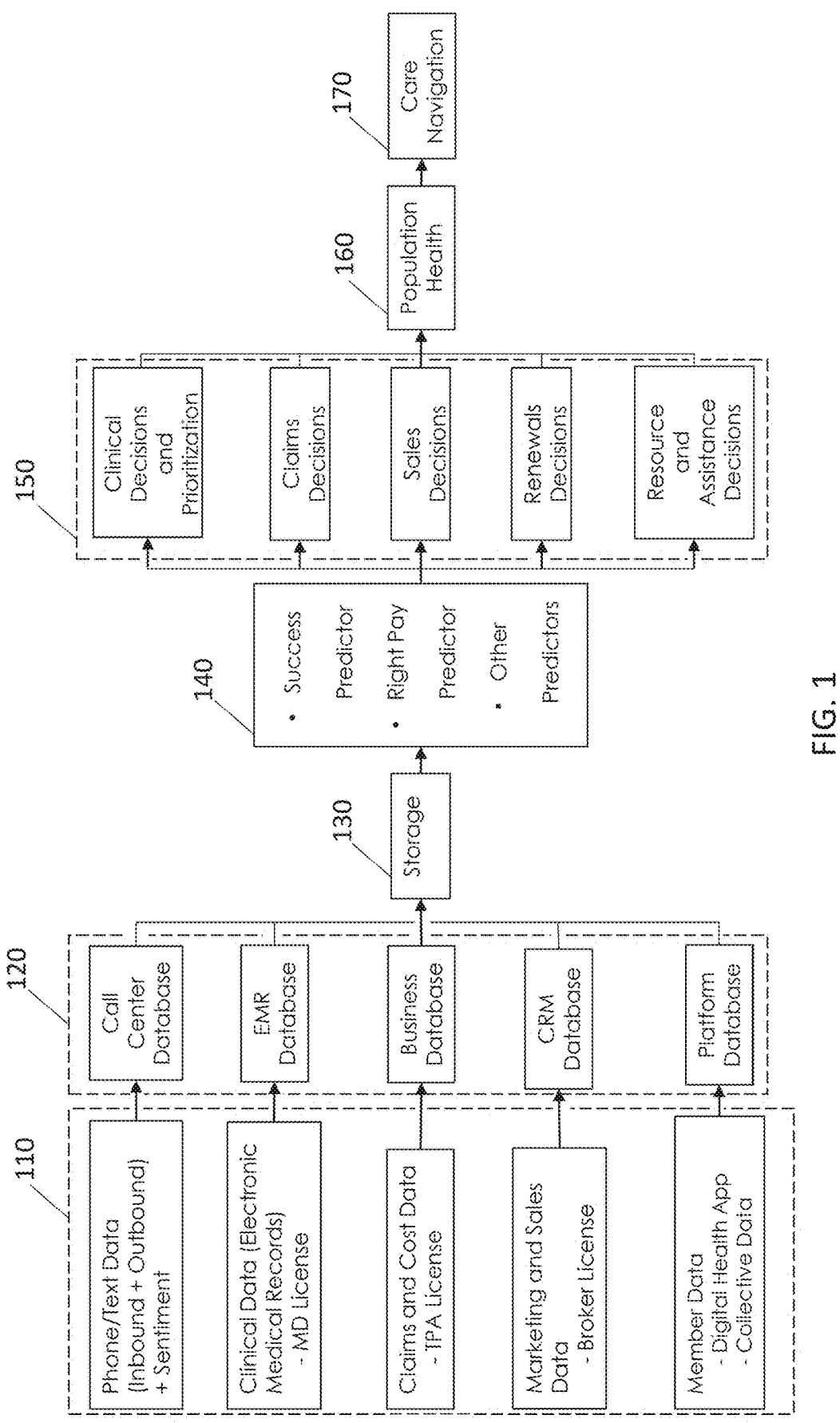
FIG. 1 is a schematic diagram of a system of the present invention.

The present invention is generally directed to systems for healthcare data aggregation and analysis, and more specifically to data aggregation systems for accessing and analyzing health data to generate dynamic predictions for healthcare solutions.

In one embodiment, the present invention includes a system for dynamic healthcare navigation, including, a server computer including a data warehouse, a memory, and a processor, and at least one database including at least one secure data set, wherein the at least one database requires at least one authorization to access the at least one secure data set, wherein the server computer is configured to implement the at least one authorization to access the at least one secure data set, wherein the server computer is configured to access the at least one secure data set and store the at least one secure data set in the data warehouse, wherein the data warehouse implements a machine learning model (MLM), wherein the MLM is configured to analyze the at least one secure data set and tag predictors within the at least one secure data set, wherein the server computer is configured to receive a request associated with the predictors within the at least one secure data set, and wherein the server computer is configured to generate an output based on the predictors within the at least one secure data set.

In another embodiment, the present invention includes a system for dynamic healthcare navigation, including a server computer including a data warehouse, a memory, and a processor, a medical database including at least one secure medical data set, an insurance database including at least one secure insurance data set, and a third-party administrator (TPA) database including at least one secure TPA data set, wherein the medical database requires a medical authorization to access the at least one secure medical data set, wherein the insurance database requires an insurance authorization to access the at least one secure insurance data set, wherein the TPA database requires a TPA authorization to access the at least one secure TPA data set, wherein the server computer is configured to implement the medical authorization, the insurance authorization, and the TPA authorization to access the at least one secure medical data set, the at least one secure insurance data set, and the at least one secure TPA data set, wherein the server computer is configured to access the at least one secure medical data set, the at least one secure insurance data set, and the at least one secure TPA data set and store the at least one secure medical data set, the at least one secure insurance data set, and the at least one secure TPA data set in the data warehouse, wherein the data warehouse implements a machine learning model (MLM), wherein the MLM is configured to analyze the at least one secure medical data set, the at least one secure insurance data set, and the at least one secure TPA data set and tag predictors within the at least one secure medical data set, the at least one secure insurance data set, and the at least one secure TPA data set, wherein the server computer is configured to receive a request associated with the predictors within the at least one secure medical data set, the at least one secure insurance data set, and the at least one secure TPA data set, and wherein the server computer is configured to generate an output based on the predictors within the at least one secure medical data set, the at least one secure insurance data set, and the at least one secure TPA data set.

In yet another embodiment, the present invention includes a method for dynamic healthcare navigation, including implementing, via a server computer, at least one medical authorization, wherein the at least one medical authorization is granted by a medical license, accessing a secure medical database, wherein the at least one medical authorization is granted and the server computer is operable to access at least one secure medical data set stored on the secure medical database, storing the at least one secure medical data set on a data warehouse of the server computer, implementing, via the server computer, at least one insurance authorization, wherein the at least one insurance authorization is granted by an insurance license, accessing a secure insurance database, wherein the at least one insurance authorization is granted and the server computer is operable to access at least one secure insurance data set stored on the secure insurance database, storing the at least one secure insurance data set on a data warehouse of the server computer, analyzing the at least one secure medical data set and the at least one secure insurance data set, identifying at least one medical predictor within the at least one secure medical data set, wherein the at least one medical predictor is associated with a healthcare treatment plan, a price of a medical service or a medical good, or a successful medical treatment method, tagging the at least one medical predictor within the at least one secure medical data set, identifying at least one insurance predictor within the at least one secure insurance data set, wherein the at least one insurance predictor is associated with a claim payment, an insurance policy, or insurance sales data, tagging the at least one insurance predictor within the at least one secure medical data set, receiving, via a user device in network connection with the server computer, a request associated with the at least one medical predictor or the at least one insurance predictor, and generating an output based on at least one medical predictor or the at least one insurance predictor.

None of the prior art discloses a platform including authorization and the necessary licensing for the compilation of data relating to personal devices and communications, personal health, insurance, healthcare marketing, and healthcare sales which is configured to incorporate the compiled data with data generated via a user interface of the platform. Further, none of the prior art discloses storing the collected data in a data warehouse in a fixed schema for the purpose of indicating predictors in the data within the context of all collected data, and further using the analyzed data to generate predictive outputs and prioritized actions.

In the wake of modern technology development, data is generated from a variety of sources. Personal data is generated via interaction with user devices, health data is generated as a result of various medical appointments, consultations, and treatments, information regarding insurance coverage, policy pricing, claims filing and evaluation, and other data such as policy marketing and sales information is digitized and stored. However, these data systems are not configured to allow the integration of data from these various sources into a single system. Licensing, access restriction, abbreviation or anonymization of data, and requirements for privacy and protection inhibit the integration of data.

The Standards for Privacy of Individually Identifiable Health Information ("Privacy Rule") establishes a set of national standards for the protection of certain health data. Access to individually identifiable records, referred to herein as protected health information (PHI), is limited by the provisions of the Health Insurance Portability and Accountability Act of 1996 (HIPAA) according to the standards established by the Privacy Rule, such that only covered entities are able to access PHI (i.e., health data). This information includes but is not limited to: past, present, or future physical or mental health or conditions of an individual; healthcare provided to an individual; the past, present, or future payment for the provision of healthcare to the individual; demographic data of the individual; individual identifiers such as name, address, birth date, or Social Security Number (SSN); and any information for which there is a reasonable basis to believe it can be used to identify an individual.

Covered entities are organizations subject to the privacy rule, including health plans (e.g., health insurance companies, health maintenance organizations (HMOs), employer-sponsored health plans, government programs that pay for healthcare, [i.e., Medicare, Medicaid, and military and veterans' health programs]), healthcare clearinghouses (i.e., entities that process nonstandard information from another entity into a standard [i.e., standard format or data content], or vice versa), and any healthcare provider who transmits health information in electronic form (e.g., doctors, clinics, psychologists, dentists, chiropractors, nursing homes, pharmacies). Additionally, a covered entity is allowed to engage a business associate to assist in the fulfillment of healthcare activities and functions. However, the covered entity must have a written business associate contract or other arrangement with the business associate that establishes specifically what the scope of the engagement of the business associate and requires the business associate to comply with HIPAA. Examples of business associates include third-party administrators, consultants that performs utilization reviews for hospitals, companies that store or destroy medical records, healthcare clearinghouses that translate a claim from a nonstandard format into a standard transaction on behalf of a healthcare provider and forward the processed transaction to payers, and independent medical transcriptionists that provide transcription services to a physician. A covered healthcare provider, health plan, or healthcare clearinghouse can be a business associate of another covered entity.

The Privacy Rule defines the circumstances in which an individual's protected heath information may be used or disclosed by covered entities, and outlines the limitations of such disclosures. A covered entity may use and disclose PHI for the purpose of the treatment, payment, and healthcare operations and activities of the covered entity, and the entity must obtain the individual's written authorization for any use or disclosure of protected health information that is not for treatment, payment, or healthcare operations, or otherwise permitted or required by the Privacy Rule. A covered entity may not use or disclose PHI, except as either the individual or a personal representative of the individual authorizes in writing, or as the Privacy Rule permits or requires (i.e., upon request by an individual for their PHI, or upon request by the U.S. Department of Health and Human Services (HHS) in compliance investigations, reviews, or enforcement actions). As a result, many covered entities such as clinics and physicians transmit abbreviated data (i.e., medical coding and classification) rather than complete PHI to health insurance entities and platforms, and provide only that information which is necessary to share in the context of individual payments.

In order to ensure that only covered entities are operable to access electronic personal health information (ePHI or EPHI) and thereby maintain the privacy of an individual, the HHS has mandated the implementation of technological security measures. The *Security Standards for the Protection of Electronic Protected Health Information* ("Security Rule") sets forth the security standards for protecting ePHI according to the provisions of HIPAA, with which all HIPAA covered entities must comply in order to ensure security and integrity of ePHI. Specifically, covered entities must: ensure the confidentiality, integrity, and availability of all ePHI the entities create, receive, maintain or transmit; identify and protect against reasonably anticipated threats to the security or integrity of the information; and protect against reasonably anticipated, impermissible uses or disclosures. The Security Rule ensures that ePHI is not available or disclosed to unauthorized persons, altered or destroyed in an unauthorized manner, and is accessible and usable on demand by authorized persons.

The Security Rule therefore requires covered entities to implement internal policies and procedures for authorizing access to ePHI based on the user or recipient's role (i.e., role-based access). However, there are no restrictions on the use or disclosure of de-identified health information, (i.e., information which neither identifies nor provides a reasonable basis to identify an individual). This de-identified information is created by removing specified identifiers of an individual (including the relatives, household members, and employers of the individual) from the electronic health record (EHR), or if a formal determination is made by a qualified statistician that the data has been satisfactorily anonymized. Aggregated, de-identified medical records are stored as database including a variety of data attributes. These attributes are used to categorize and compile medical records into various aggregated lists based on certain attributes, such as patient diagnoses or medication regimens. These lists are operable to be sold, used, and disclosed without restriction by the Privacy Rule. However, neither PHI nor de-identified data includes personal device data, individual insurance policy data, or policy marketing and sales data.

In order to access PHI, and further to access data that is not included in the PHI of an individual, such as personal device data, specific insurance information regarding claims, policy pricing, and policy coverage, and marketing and sales data regarding various insurance plans and policies, an entity must obtain the necessary licensure or documentation to verify the role of the entity (e.g., as a covered insurance entity or licensed insurance broker). The system of the present invention advantageously incorporates multifaceted authorization granted by a variety of licenses to access data from a variety of databases, integrate the information into a single data warehouse, and analyze the information in context with other data sources that are not fully integrated according to the systems of the prior art.

Insurance licensure varies by state and is dependent on the products or services offered by an entity or individual, as well as the residence of the individual licensee. Individual licensees include insurance agents, also referred to as insurance producers, as well as insurance brokers and third party administrators (TPAs). Insurance agents are licensed to sell forms of insurance on behalf of an insurance company, while insurance brokers represent an individual and identify the best insurance policy to meet the needs of the individual, often at the best price. A TPA is an individual or entity who obtains or implements coverage of, underwrites, collects charges or premiums from, or adjusts or settles claims in connection with life or health insurance. License types for insurance licensees include a resident license, a non-resident license, and a non-resident adjuster license. These license types incorporate a variety of sub classes for each type, depending on the state in which the license is registered and the function of the licensee. License classes include a producer license, agent license, broker license, adjustor license, consultant license, managing general agent license, and third party administrator license.

A health insurance business (i.e., an insurance entity or agency) generally requires a corporation or partnership license to permit the business entity to participate in the business of insurance. In some states, no Lines of Authority (LOA) are generally assigned to the business entity license. That is to say, the business is not licensed to practice in a particular subject area of insurance. In such cases, the lines of authority (e.g., "Accident and Health or Sickness" line, "Life and Health" line) for the insurance business come from the individual licensees. Thus, for an insurance business to offer healthcare insurance, an agent registered in the Accident and Health or Sickness LOA must be registered in association with the insurance business.

Health maintenance organizations (HMOs) are health insurance organizations to which subscribers pay a predetermined fee in return for a range of medical services from physicians and healthcare workers registered with the organization. HMOs must have an HMO License in order to provide services to subscribers. Similarly, preferred provider organizations (PPOs) are health insurance organizations to which subscribers pay a predetermined fee in return for a range of medical services from physicians and healthcare workers. However, the physicians and healthcare workers may not be registered with the organization. PPOs must have a contract with a licensed insurer (e.g., an agency) in order to offer services to subscribers.

Individual healthcare practitioners are required to obtain a medical license before they are legally able to practice medicine and thereby obtain PHI from individuals. In the United States, medical licenses are usually granted by individual states. Only those with medical degrees from schools listed in the World Directory of Medical Schools are permitted to apply for medical licensure. A medical license (MD) is granted on an individual basis to practitioners in a variety of fields (e.g., doctors, psychiatrists, dentists, neurologists, oncologists, dermatologists).

A majority of covered entities contain only the licensing necessary for functioning as a single covered entity. For example, an insurance entity does not obtain both an insurance license and a medical license. Therefore, the insurance entity is not authorized to access all data relating to a patient's medical file. However, the system of the present invention incorporates a variety of individual and entity licensures which provide the necessary authorization to access ePHI and eMR (i.e., electronic medical records). The system then incorporates the gathered information into a data warehouse, and analysis the combined data using predictive analytics in combination with prediction tools to indicate predictors in the data in order to identify patient needs, population health trends, insurance policy pricing and coverage, and more. These identified factors and decisions are then used to generate a public health output for supporting public health decisions.

Data Combination

The system of the present invention aggregates and integrates data from a variety of sources in order to generate predictive outcomes for use in public health and healthcare navigation in a multi-step process. As disclosed herein, some databases require a specialized license to enable the storage and access of the data. The system of the present invention incorporates multifaceted authorization to access and combine data, including health data, from multiple databases.

In one embodiment, the present invention incorporates authorization provided by a medical license in order to access electronic medical records (EMR). In one embodiment, the medical licensing process implements authorization software which provides for the necessary authorization to access electronic medical records (EMR) stored on a database, transfer the private clinical data disclosed therein to a data warehouse for aggregation with data from other sources, and organize and store the data in the data warehouse. In one embodiment, the medical license is a medical license implemented by a physician user within the system. The physician user is operable to access EMR via an EMR system comprising an EMR database. The EMR data is then transmitted from the EMR system database to the data warehouse of the present invention. In one embodiment, the EMR system is a cloud-based EMR system. In one embodiment, the EMR system is a MAC-based EMR system. In one embodiment, the EMR system is certified by the Office of the National Coordinator for Health Information Technology (ONC Certified). In one embodiment, the EMR system is a behavioral/mental health EMR system. In one embodiment, the EMR system is a medical billing EMR system.

In one embodiment, the present invention includes a third party administrator (TPA) licensing process. In one embodiment, the TPA licensing process implements authorization software which provides for the necessary authorization to access financial information and claims data stored on a database, transfer the financial information and claims data to a data warehouse for aggregation with data from other sources, and organize and store the data in the data warehouse.

In one embodiment, the present invention includes a broker licensing process. In one embodiment, the broker licensing process implements authorization software which provides the necessary authorization to access employment records (e.g., employer data, employee data) and insurance data stored on a database, transfer the records disclosed therein to a data warehouse for aggregation with data from other sources, and organize and store the data in the data warehouse.

In one embodiment, the present invention implements one or more software systems configured to perform one or more pharmaceutical tasks and/or generate an output relating to a pharmaceutical task. In one embodiment, the present invention implements and/or accesses one or more smart formularies. As used herein, the term "smart formulary" refers to a digital list of generic and brand name prescription drugs covered by a health plan generated using one or more artificial intelligence models. In one embodiment, the present invention is configured to aggregate prescription cost and insurance claims relating thereto. In one embodiment, the system of the present invention is configured to generate one or more outputs based on information received from a digital formulary or smart formulary.

In one embodiment, the present invention is configured to access a variety of human resource data provided by one or more businesses associated with a specific user. In this way, the system of the present invention is operable to verify employment, insurance plan activity, and evaluate the coverage options available to a user. In one embodiment, the system implements authorization software which provides the necessary authorization to access employment records (e.g., employer data, employee data) stored on a database, transfer the records disclosed therein to a data warehouse for aggregation with data from other sources, and organize and store the data in the data warehouse.

In one embodiment, the system of the present invention acquires data manually through a request and response system. In one embodiment, the system of the present invention automatically extracts data from a variety of databases. This automatic retrieval of information is enabled by the multi-faceted authorization provided by the numerous licensures implemented via the system of the present invention.

Decision Support and Analysis

Upon combination and integration of the data from various data sources into the data warehouse of the present invention, the system of the present invention processes and analyzes the combined data to identify and indicate predictors within the data. In one embodiment, this is accomplished via the use of a machine learning model. In one embodiment, the machine learning model is incorporated into a natural language processing system. A machine learning model is a program that is configured to identify patterns, categorize data, and make decisions based on a dataset. For example, the system of the present invention is operable to access and store large datasets relating to insurance policy claims pricing. The machine learning model of the present invention is operable to analyze these datasets to identify a variety of factors, including but not limited to a policy price related to a specific diagnosis, claim type, or treatment, coverage provided by a specific claim, claims price dependent on various machinery implemented during the diagnosis and treatment process, and coverage provided by various claims. In natural language processing systems, machine learning models are configured to parse and correctly recognize the intent behind sentences or combinations of words. In one embodiment, the system utilizes an NLP engine and additional semantic analysis to recognize keywords, phrases, and ideas within a data set (e.g., doctor's notes saved within a patient file). Keywords, phrases, and ideas are identified and tagged within the data set.

In one embodiment, the predictors are used to indicate the success of a treatment plan or series of successive medical treatments which lead to a favorable outcome in the context of the gathered data. For example, the system of the present invention is operable to identify a plurality of treatment plans within the data set associated with users diagnosed with fibromyalgia. The system then identifies the success of each treatment plan, with a combination of medication, cognitive behavioral therapy, and chiropractic treatment being the most effective (e.g., resulting in the lowest number of return visits to a physician seeking relief from the symptoms of fibromyalgia) and a simple recommendation to increase physical activity being the least effective (e.g., resulting in the highest number of return visits to a physician seeking relief from the symptoms of fibromyalgia). The system then analyzes the treatment plan suggested by a physician user for a target patient user diagnosed with fibromyalgia, which consists of a combination of medication and chiropractic treatment. The system then generates a predicted success rate of the suggested treatment plan based on a comparison between the suggested plan and both the most and least effective treatment plans identified within the data.

In one embodiment, the predictors are used to indicate the right payment for a medical device, good, service, or claim in the context of the gathered data. The system of the present invention evaluates the analyzed data to identify one or more predictors which are used to tag payment data. The system of the present invention also evaluates the analyzed data to identify one or more predictors which are used to tag a specific medical device, good, service, or claim. The system evaluates the data tagged with a target medical device, good, service, or claim and the prices associated with the target medical device, good, service, or claim in order to identify an optimal payment for the target medical device, good, service, or claim for a specific user.

In one embodiment, the predictors are used to create one or more series of dynamically generated actions which, in series, provide a strategic schema for addressing one or more health concerns. For example, the system of the present invention is operable to identify a plurality of treatment plans within the data set associated with users diagnosed with fibromyalgia. The system then identifies the success of each treatment plan, with a combination of medication, cognitive behavioral therapy, and chiropractic treatment being the most effective (e.g., resulting in the lowest number of return visits to a physician seeking relief from the symptoms of fibromyalgia) and a simple recommendation to increase physical activity being the least effective (e.g., resulting in the highest number of return visits to a physician seeking relief from the symptoms of fibromyalgia). The system then evaluates the coverage provided by the users insurance policy, which includes medical care and cognitive behavioral therapy, but not chiropractic treatment. In one embodiment, the system is configured to suggest a cost-effective treatment plan for the user, which includes medication and cognitive behavioral therapy, but not chiropractic treatment. In one embodiment, the system is configured to suggest a cost-effective treatment plan for the payer (i.e., the insurance company), which includes medication, but not cognitive behavioral therapy or chiropractic treatment.

In one embodiment, the predictors are used to indicate a renewal rate for an insurance policy or claim in the context of the gathered data. A renewal rate measures the proportion of insurance users who opt to renew and extend their insurance policy at the end of a subscription period. The present invention is operable to access insurance data and analyze the data to tag predictors for insurance policy information, including dates associated with the initiation, extension, and termination of one or more insurance policies. The system then analyses the tagged data to determine a renewal rate for various insurance policies and providers.

Healthcare Access and Delivery

In one embodiment, the present invention generates care logistics relating to population health, referral management, and care navigation. In one embodiment, the system of the present invention is configured to evaluate pricing and coverage based on specific medical equipment implemented by various healthcare providers within the system. For example, when evaluating a referral for an MRI to obtain X data, the system if the present invention evaluates the data associated with a first clinic and a second clinic. The first clinic utilizes a brand new MRI machine, which produces data relating to X, Y, and Z and costs $1200. The second clinic utilizes an older model MRI machine, which produces data relating to X only and costs $400. The system then identifies that for the purpose of obtaining X data, the second clinic will be the less expensive option and suggests the second clinic to a user (i.e., a patient user, physician user, or insurance user).

In one embodiment, the system of the present invention is configured to generate one or more reminders based on the care provided by an insurance plan or policy and a specified timeframe before policy renewal (e.g., one month, 90 days, three months, etc.). For example, an exemplary insurance plan covers a visit to an optometrist. However, the user associated with the plan has not made an appointment with the optometrist and the end of the policy cycle is within a specified timeframe of 90 days before policy renewal. The system of the present invention is then configured to generate a notification including a reminder that the user has one unused optometrist appointment left in their plan. The system then transmits and displays the notification to a GUI of a device associated with a specific user.

In one embodiment, the present invention allows for the selection of one or more prescriptions based on a predicted price of the prescription generated by the system of the present invention. As disclosed herein, the system of the present invention is configured to incorporate on or more formularies (i.e., smart formularies or digital formularies) into the data warehouse of the present invention. These formularies are operable to be produced by a variety of sources, including pharmaceutical companies, regulatory agencies, pharmacies, and the system of the present invention itself based on the aggregated data. The system is configured to access one or more formularies and identify the least expensive medication for an intended use. Factors which affect medication pricing include but are not limited to efficacy, market competition, scarcity, delivery route, transportation cost, and retail profit margins. The smart formularies and digital formularies of the present invention are configured to incorporate on or more of these factors into the development of the formulary. Additionally, in one embodiment, the system of the present invention is configured to identify the most cost effective medication based on one or more of these factors.

In one embodiment, the present invention provides a network for collecting copays and deductibles. In one embodiment, the system of the present invention implements online transaction software for enabling remote transactions (e.g., wire-transfers, e-commerce payment systems). Examples of remote transactions include but are not limited to direct deposit payments, direct debit payments, electronic bill payments, wire transfers, digital payments completed via digital payment applications, and e-commerce payments. In one embodiment, the system of the present invention displays an expected cost before and after insurance coverage. In one embodiment, the system of the present invention is configured to incorporate various payment substitutions such as coupons and incentives provided by one or more third parties.

Paying Providers and Risk Pool Management

The system of the present invention implements online transaction software configured to enable remote transactions as disclosed herein. Examples of remote transactions include but are not limited to direct deposit payments, direct debit payments, electronic bill payments, wire transfers, digital payments completed via digital payment applications, and e-commerce payments.

One of ordinary skill in the art will understand the structure and function of a "risk pool" as described herein. A risk pool is a group of people covered by a healthcare insurance plan. Insurance plans evaluate the financial history and health status of the risk pool to estimate future healthcare costs. Pooling risks together allows the costs of those at higher risk of high medical costs to be subsidized by those at lower risk. In the system of the present invention, one or more businesses (e.g., a small business) contribute a set amount of money (i.e., a fund) to cover the healthcare expenses of the users within the risk pool. An insurance company or broker manages the fund, allocating payment based on the coverage provided by one or more policies which cover the risk pool.

In one embodiment, the present invention is configured to generate a summary of one or more costs associated with a healthcare solution. In one embodiment, the summary is a summary of the total cost of proposed healthcare solutions not covered by an insurance plan (i.e., "out-of-pocket" costs). In one embodiment, the summary of the total out-of-pocket costs generated by the present invention is transmitted to the user device. In one embodiment, the summary of the cost is a summary of the cost of the proposed healthcare solution which an insurance provider is required to cover. In one embodiment, the system is in network connection with a user device and is configured to transmit one or more communications to the user device (i.e., a user device of a patient user, a user device of an insurance user).

Collaborative Products for Communities

The system of the present invention provides for treatment plan development, evaluation, insurance coverage, prescription fulfillment and cost reductions, and other healthcare solutions. In one embodiment, the system of the present invention is configured to dynamically generate predictions and suggests relating to a group of users, referred to herein as a community. In one embodiment, the system is operable to incorporate healthcare data relating to a range of users both inside and outside the community, tag predictors in the data, and utilize the tagged predictors to generate predictions and suggestions relating to healthcare as described herein with regard to the community.

In one embodiment, the present invention is operable to generate predictions and suggestions relating to healthcare as described herein with regard to a single user. In one embodiment, the present invention is operable to generate predictions and suggestions relating to healthcare as described herein with regard to a community of users. In one embodiment, the community includes about 2-19 users. In one embodiment, the community includes between about 20-49 users. In one embodiment, the community includes more than 20 users. In one embodiment, the community includes between about 50-200 users. In one embodiment, the community includes between about 50-1000 users. In one embodiment, the community includes more than 50 users. In one embodiment, the community includes less than 200 users. In one embodiment, the community includes less than 500 users.

In one embodiment, the communities of the present invention comprise users who are not covered under an insurance plan in a country (e.g., the United States) but are traveling and spending an extended period of time in the country. The present invention provides dynamic healthcare options for the communities of the present invention based on the needs of the community rather than a revenue-based flat rate. The present invention advantageously provides for dynamic identification of the most cost effective healthcare solutions for a community.

In one embodiment, the system of the present invention provides for end-to-end franchise management of healthcare institutions including clinical evaluation, insurance coverage, supply chain management, pharmaceutical communication, claims evaluation, and payment processing.

Other

In one embodiment, the present invention enable the creation of self-organizing communities (e.g., associations, families, neighborhoods, towns, chambers, etc.). In one embodiment, the system of the present invention builds a healthcare plan based on the inputs from one or more user devices associated with a user of the system of the present invention. In one embodiment, one or more community members input the goals, requirements, and budget of the community into the system of the present invention via a user device. The present invention is configured to use these input goals, requirements, and budget as parameters for dynamic generation of suggestions and predictions. In one embodiment, the present invention is configured to evaluate the inputs and changes to the input parameters over time to generate a predictive model for input evolution. In one embodiment, the system of the present invention utilizes the input parameters and./or the predictive model for input evolution to generate a solution which meets an input need within the community. In this way, a community is able to pay for only those services which are essential requirements without requiring extraneous, costly coverage for unnecessary services, as in the case of bundle packages according to systems of the prior art.

In one embodiment, the system of the present invention is configured to generate one or more contracts though the use of artificial intelligence and natural language processing. In one embodiment, the present invention is configured to generate a narrative summary of benefits and coverage (SBC) for one or more healthcare solutions suggested using the system of the present invention. In one embodiment, the present invention is configured to generate a narrative summary plan description (SPD) for one or more healthcare solutions suggested using the system of the present invention. The SPD of the present invention provides a detailed guide to the benefits included in the healthcare solution generated by the present invention (e.g., a healthcare plan) and how the plan works. In one embodiment, the SPD describes when community members become eligible to participate in the plan, how benefits are calculated and paid, how to claim benefits, and when benefits become vested.

In one embodiment, the present invention includes one or more processes to create and/or alter the design of the system or the data organized therein based on gathered and analyzed data and/or feedback from previously generated outputs. This creation and/or alteration influences and/or changes the generated output in future predictive analysis. The artificial intelligence model used by the present invention is trained using generated predictions and feedback from those predictions. In one embodiment, upon generation of a solution, the system of the present invention analyzes one or more actions taken by a user (i.e., feedback) upon receiving the generated solution to determine if the generated prediction was favorable. In one embodiment, the user selects an interactive button, switch, icon, notification, or other selectable feature to accept the generated solution. This favorable outcome is then fed back into the system and used to continuously and automatically train the artificial intelligence engine implemented by the system of the present invention. Feedback of a favorable outcome skews the artificial intelligence engine to weigh similar outcomes with more positive weight than an alternative suggestion. For example, the system of the present invention receives a request from a user for a healthcare solution for a twisted ankle that is less than $200 and includes a geographic parameter of being within 25 miles of the user device based on a global positioning software. A first outcome generated in response to the request includes a link to purchase a $100 ankle brace, a $25 ice pack, and a $25 elastic bandage, and further includes a series of treatment steps to rest the ankle, ice the ankle, apply the elastic to the sprained ankle, and elevate the injury. A second outcome generated in response to the request includes a coupon for a $75 examination by a physician at a clinic that is located within a 25 mile radius of the user device. The user selects the first option, cause the system to weight the first option as more favorable for other users, such as other users within a similar age range, socio-economic demographic, and/or community.

Referring now to the drawings in general, the illustrations are for the purpose of describing one or more preferred embodiments of the invention and are not intended to limit the invention thereto.

FIG. 1 is a schematic diagram of a system of the present invention. Data is generated from a variety of data sources 110. The generated data is stored on a variety of databases 120, corresponding to the source of the database. The present invention accesses each of the databases 120 and stores the accessed data in a data warehouse 130. The system of the present invention then uses predictive analytics in combination with prediction tools 140 to indicate predictors in the data. The indicated predictors are then analyzed in context of an inquiry to generate a supported decision 150 for a variety of applications. These supported decisions are then used to generate a public health output 160 for supporting public health decisions. The system then uses the public health output 160 to generate a healthcare navigation output 170 for navigating healthcare options.

The system of the present invention aggregates and integrates data from a variety of sources in order to generate predictive outcomes for use in public health and healthcare navigation in a multi-step process. In the first step, data is generated from a variety of sources. In the second step, the generated data is stored on a database corresponding to the source of the data. In the third step, the system of the present invention accesses, combines, and stores the data in a data warehouse. As disclosed herein, some databases require a specialized license to enable the storage and access of the data. The system of the present invention advantageously incorporates multifaceted authorization to access and combine data, including health data, from multiple databases.

Examples of data gathered and used by the system of the present invention include but are not limited to instant messaging data, browsing history, location data, video data, audio data, image data, text data, clinical data (e.g., electronic medical records [EMR], ePHI), claims data, cost data, insurance data, marketing data, sales data, data generated from a subscription to a platform, and data generated from a profile on a mobile app. In one embodiment, the data of the present invention is generated by a variety of sources, including but not limited to one or more personal devices (e.g., a cell phone, a computer), TPAs, HMOs, insurance providers (e.g., agents, brokers, agencies), and interactive user interfaces, platforms, and portals hosted either remotely (e.g., on a cloud servers) or locally (e.g., a physical server).

In one embodiment, the data of the present invention is stored on a database after generation. In one embodiment, the data of the present invention is stored on a database specific to the source of the data (e.g., the database used to store ePHI is not the database used to store personal device data). In one embodiment, the system of the present invention is configured to access multiple databases in order to access the data. In one embodiment, the system of the present invention accesses the database in real time upon generation of data.

In one embodiment, the system of the present invention gathers personal device data (e.g., inbound and outbound communications) generated by a personal user device. In one embodiment, personal user device data is collected using call center software and stored in an associated database. In one embodiment, the call center software implemented by or integrated with the system of the present invention includes at least on artificial intelligence engine capable of natural language processing (NLP) and semantic categorization of audio or speech-to-text audio. In one embodiment, the call center software analyzes incoming and outgoing calls in real time to provide semantic analysis of personal user device data. In one embodiment, personal device data is stored on a call center database (e.g., a cloud server in network connection with the call center software). In one embodiment, a personal device is in network connection with a remote or local database, and the personal device data generated by the device is stored on the remote or local database.

In one embodiment, the system of the present invention gathers electronic medical records (EMR) including PHI and/or de-identified data as disclosed herein. In one embodiment, electronic medical records are stored on a healthcare database (e.g., a cloud server in network connection with a device used by a healthcare clinic, physician, etc.). In one embodiment, a user device utilized by a healthcare provider (e.g., doctors, clinics, psychologists, dentists, chiropractors, nursing homes, pharmacies) is in network connection with a remote or local database, and the personal device data generated by the device is stored on the remote or local database.

In one embodiment, the system of the present invention gathers insurance data, including but not limited to past and present insurance claims, policy pricing, and policy coverage. In one embodiment, the insurance data includes identifiable information relevant to an individual and/or individual policy. In one embodiment, insurance data is stored on an insurance database (e.g., a cloud server in network connection with a device used by an insurance entity). In one embodiment, a user device utilized by an insurance entity (e.g., agent, TPA) is in network connection with a remote or local database, and the personal device data generated by the device is stored on the remote or local database.

In one embodiment, the system of the present invention gathers marketing and sales data related to various insurance policies, plans, offerings, and organizations (e.g., HMOs, PPOs) data. In one embodiment, marketing and sales data is stored on a broker database (e.g., a cloud server in network connection with a device used by an insurance broker). In one embodiment, a user device utilized by an insurance broker is in network connection with a remote or local database, and the personal device data generated by the device is stored on the remote or local database.

In one embodiment, the system of the present invention includes a user interface platform including at least one user account. In one embodiment, user account information is stored on a platform database (e.g., a cloud server in network connection with a user device which accesses the platform). In one embodiment, the user device is in network connection with a remote or local database, and the personal device data generated by the device is stored on the remote or local database.

Upon combination of the data from various data sources into the data warehouse of the present invention, the system of the present invention, in a fourth step, processes and analyzes the combined data to identify and indicate predictors within the data. In one embodiment, the predictors are used to indicate the success of a treatment plan in the context of the gathered data, a serious of successive medical treatments which lead to a favorable outcome, the right payment for a medical device, good, or service, and other predictors.

In one embodiment, the system of the present invention includes at least one artificial intelligence engine. In one embodiment, the at least one artificial intelligence engine is implemented via a neural network for system analysis of data and dynamic evaluation. The system is operable to utilize a plurality of learning techniques including, but not limited to, machine learning (ML), artificial intelligence (AI), deep learning (DL), neural networks (NNs), artificial neural networks (ANNs), support vector machines (SVMs), Markov decision process (MDP), and/or natural language processing (NLP). The system is operable to use any of the aforementioned learning techniques alone or in combination.

Further, the system is operable to utilize predictive analytics techniques including, but not limited to, machine learning (ML), artificial intelligence (AI), neural networks (NNs) (e.g., long short term memory (LSTM) neural networks), deep learning, historical data, and/or data mining to make future predictions and/or models. The system is preferably operable to recommend and/or perform actions based on historical data, external data sources, ML, AI, NNs, and/or other learning techniques. The system is operable to utilize predictive modeling and/or optimization algorithms including, but not limited to, heuristic algorithms, particle swarm optimization, genetic algorithms, technical analysis descriptors, combinatorial algorithms, quantum optimization algorithms, iterative methods, deep learning techniques, and/or feature selection techniques.

Neural networks, also known as artificial neural networks (ANNs) or simulated neural networks (SNNs), are a subset of machine learning and are at the heart of deep learning algorithms. Their name and structure are inspired by the human brain, mimicking the way that biological neurons signal to one another. Artificial neural networks (ANNs) are comprised of node layers, comprising an input layer, one or more hidden layers, and an output layer. Each node, or artificial neuron, connects to another and has an associated weight and threshold. If the output of any individual node is above the specified threshold value, that node is activated, sending data to the next layer of the network. Otherwise, no data is passed along to the next layer of the network.

Neural networks utilize training data to learn and improve their accuracy over time through repeated output generation and feedback. Once these learning algorithms are fine-tuned for accuracy, they are powerful tools in computer science and artificial intelligence, allowing for the classification and clustering of data at a high velocity. The timeframe for speech and image recognition and text analysis is significantly reduced by neural networks when compared to manual identification by human experts.

In some exemplary embodiments, each individual node is an individual linear regression model, composed of input data, weights, a bias (or threshold), and an output. Once an input layer is determined, weights are assigned. These weights assist in the determination of the importance of any given variable, with larger ones contributing more significantly to the output compared to other inputs. All inputs are then multiplied by their respective weights and then summed. Afterward, the output is passed through an activation function, which determines the output. If that output exceeds a given threshold, it "fires" (or activates) the node, passing data to the next layer in the network. This results in the output of one node becoming the input of the next node. This process of passing data from one layer to the next layer defines this neural network as a feedforward network. Larger weights signify that particular variables are of greater importance to the decision or outcome.

Deep neural networks are operable to flow unidirectionally from input to output (i.e., a feedforward configuration). However, deep neural network models are further operable to be trained through backpropagation; that is, move in the opposite direction from output to input. Backpropagation allows for the calculation and attribution of an error associated with each neuron, allowing for the appropriate adjustment of the parameters of the model(s).

In machine learning, backpropagation is an algorithm for training feedforward neural networks. Generalizations of backpropagation exist for other artificial neural networks (ANNs), and for functions generally. These classes of algorithms are all referred to generically as "backpropagation". In fitting a neural network, backpropagation computes the gradient of the loss function with respect to the weights of the network for a single input-output example, and does so efficiently, unlike a naive direct computation of the gradient with respect to each weight individually. This efficiency makes it feasible to use gradient methods for training multilayer networks, updating weights to minimize loss; gradient descent, or variants such as stochastic gradient descent, are used. The backpropagation algorithm works by computing the gradient of the loss function with respect to each weight by the chain rule, computing the gradient one layer at a time, iterating backward from the last layer to avoid redundant calculations of intermediate terms in the chain rule; this is an example of dynamic programming. The term backpropagation strictly refers only to the algorithm for computing the gradient, not how the gradient is used; however, the term is often used loosely to refer to the entire learning algorithm, including how the gradient is used, such as by stochastic gradient descent. Backpropagation generalizes the gradient computation in the delta rule, which is the single-layer version of backpropagation, and is in turn generalized by automatic differentiation, where backpropagation is a special case of reverse accumulation. In one embodiment, the system of the present invention receives a request for an output based on input information. The system of the present invention analyzes the data, including the identified and tagged predictors within the data, to generate a supported decision based on the identified predictors.

FIGS. 2-13 illustrate exemplary GUI displays of a platform which incorporates the system of the present invention. Various functionalities of the platform are enabled by the system disclosed herein which provides data analysis relating to insurance pricing, healthcare planning, and treatment options. The display is configured to receive an input from a user via touch select functionality or click select functionality, for web browser embodiments of a platform which incorporates the system of the present invention.

Figure 2:
FIG. 2 is an exemplary Graphical User Interface (GUI) display of a platform of the present invention.

The platform is operable to facilitate a variety of functions as shown in the GUI of FIG. 2. The GUI is operable to receive a request to schedule an appointment, refill a prescription, view and share a membership and prescription card, view and share benefits and coverage information, pay a user account through the system, upload billing information and access receipts for previous payments, access the out-of-pocket summary generated by the system of the present invention, and update the information maintained by the system. However, the functionality provided by the system of the present invention through the platform is not limited to only these functions. The system enables a wide range of functions based on the variety of data which is acquired and analyzed in order to provide the most accurate healthcare coverage.

Figure 3:
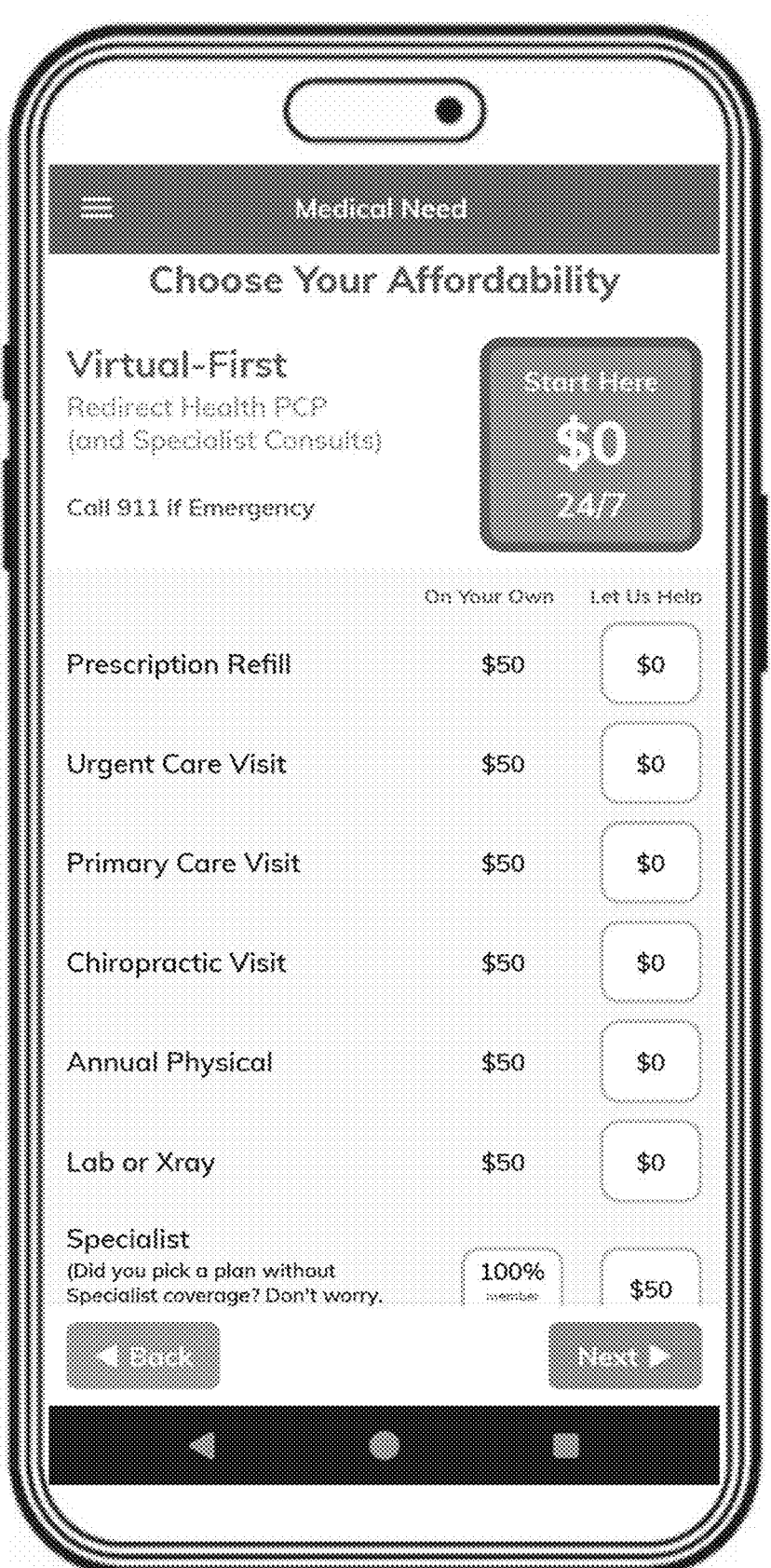
FIG. 3 is an exemplary GUI display of a platform of the present invention.
Figure 4:
FIG. 4 is an exemplary GUI display of a platform of the present invention.

The platform of the present invention is operable to provide interaction with service providers for a user to meet their medical needs. As illustrated in FIG. 3, the platform is able to generate a side-by-side comparison of the identified cost for a variety of medical goods and services based on coverage options. The system is operable to dynamically suggest the most common medical goods and services required by users within a group (e.g., users within a single risk pool or users within a certain age demographic). As illustrated in FIGS. 4-5, the system is further operable to receive on or more inputs via touch screen, typed response, or drop-select functionality to identify a required medical service based on the onset of symptoms, the general nature of symptoms, and other input information.

Figure 6:
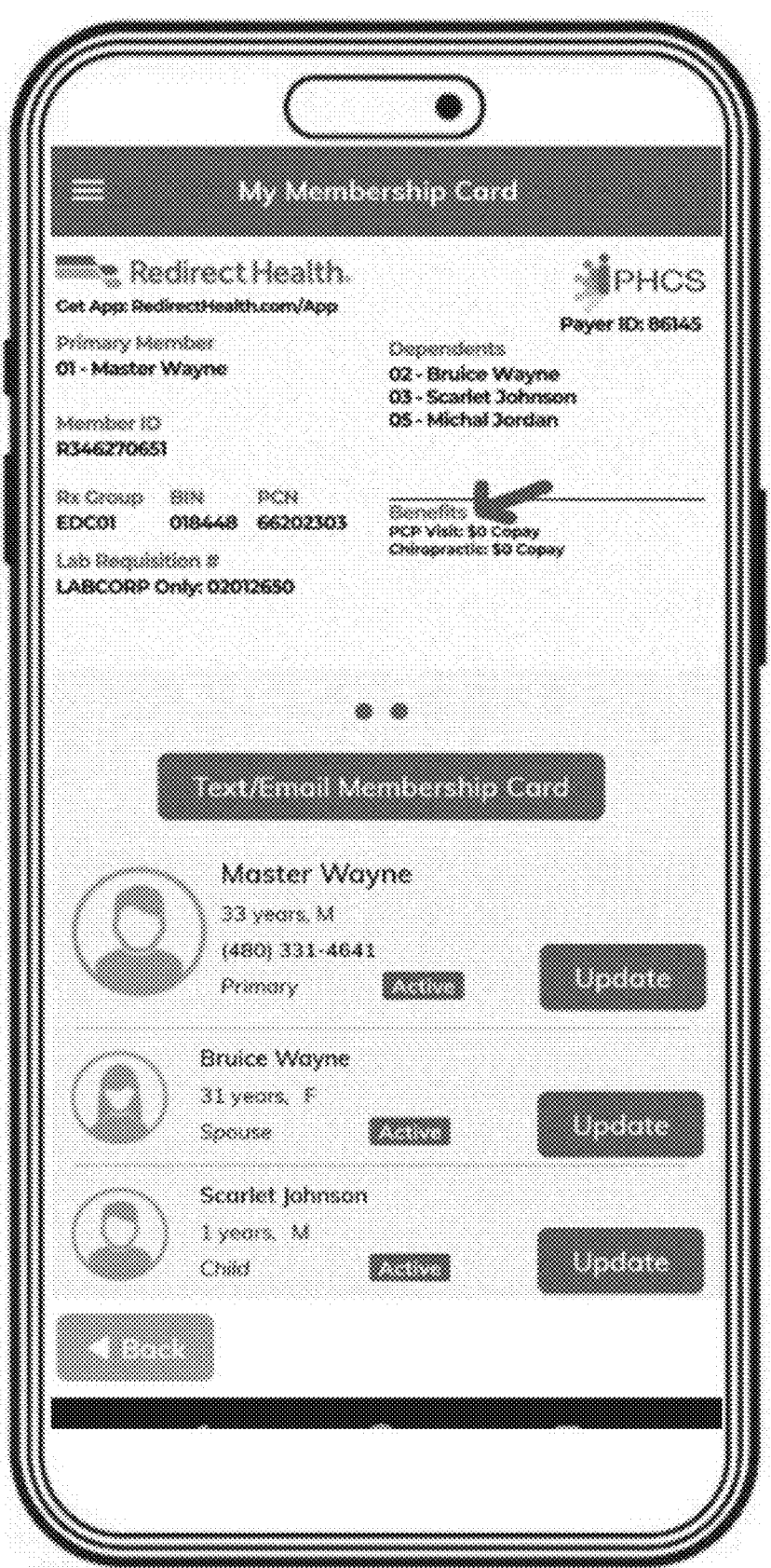
FIG. 6 is an exemplary GUI display of a platform of the present invention.

The GUI is operable to display a membership and prescription card for a user account as illustrated in FIG. 6, which displays membership information including but not limited to primary member name, dependent member name, member ID number, prescription group, Bank Identification Number (BIN), Processor Control Number (PCN), benefits, and lab requisition number. The membership and prescription card is operable to be wirelessly transmitted to a member within a network of a user in order to enable a plurality of users associated with a single member to access and utilize the system of the present invention.

Figure 7:
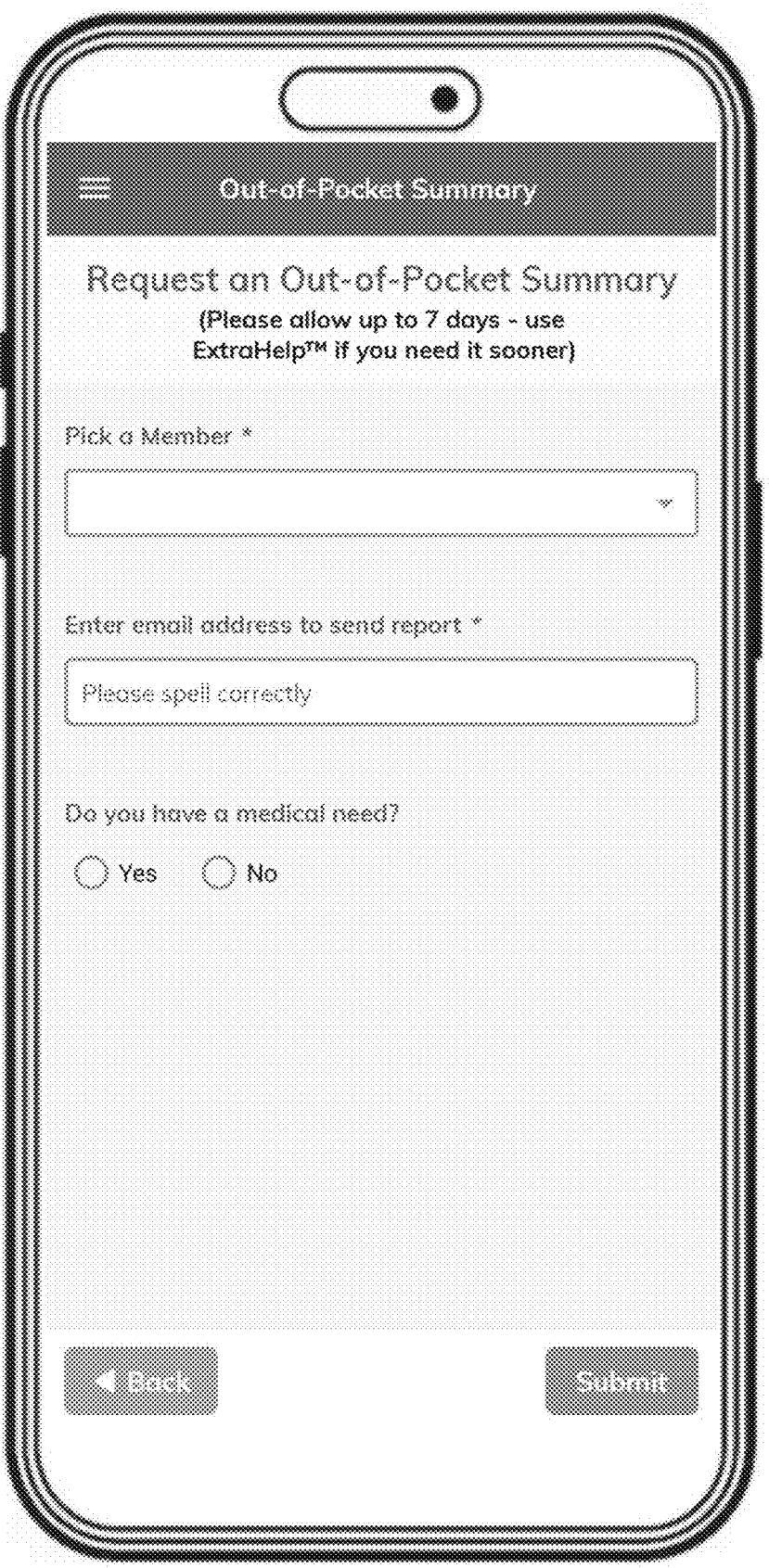
FIG. 7 is an exemplary GUI display of a platform of the present invention.
Figure 8:
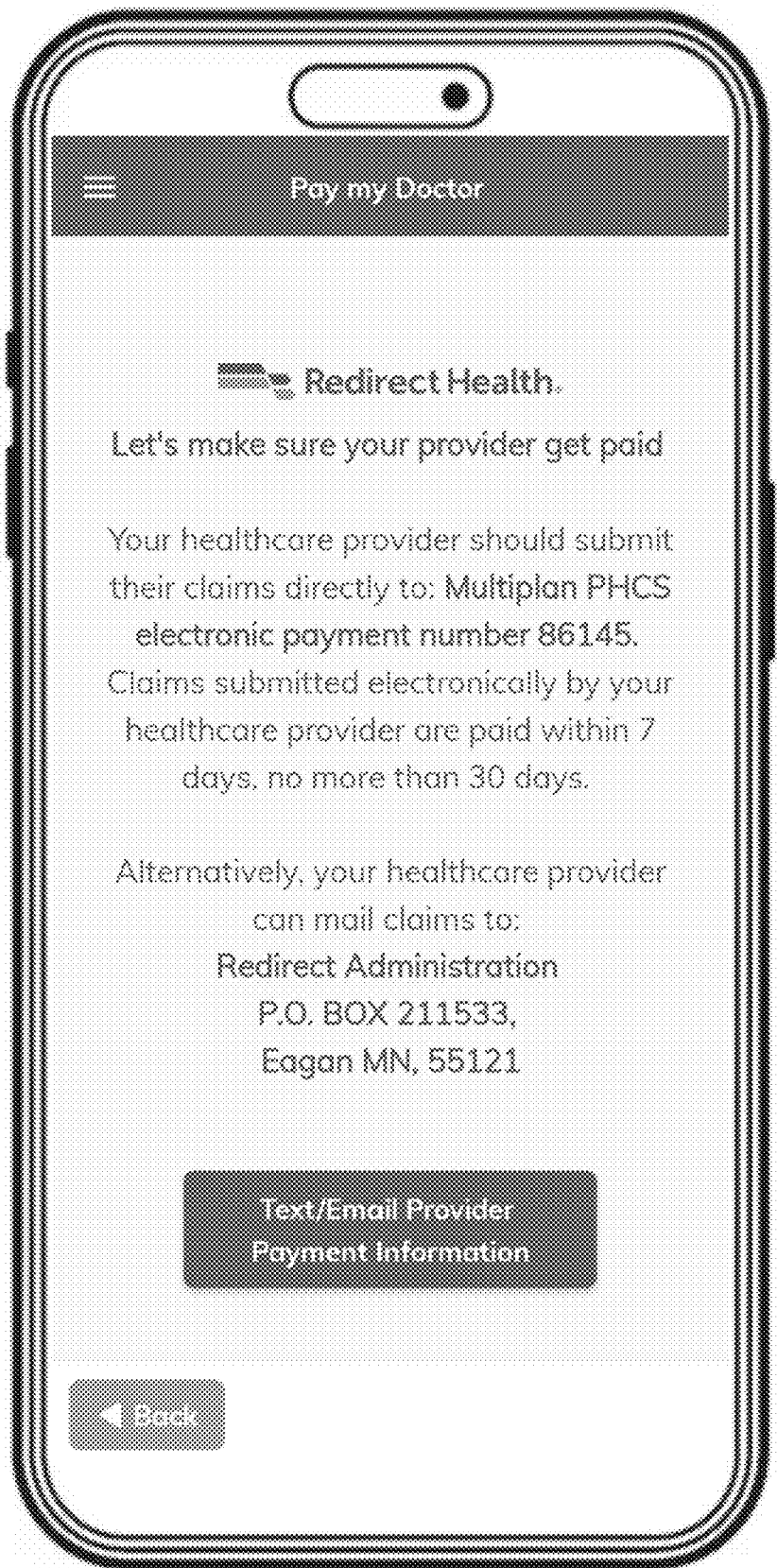
FIG. 8 is an exemplary GUI display of a platform of the present invention.

The GUI is operable to display an out-of-pocket summary as disclosed herein. The system is configured to initiate the transmission of the summary upon receiving an email, a phone number, a fax number, or other contact information from a user as illustrated in FIG. 7. The system is further configured to adapt an out-of-pocket summary generated relating to an insurance policy based on the member for which the medical good or service was provided. FIG. 8 depicts a payment information messaging portal which enables the system of the present invention to receive and provide payment based on provided medical goods and services.

Figure 9:
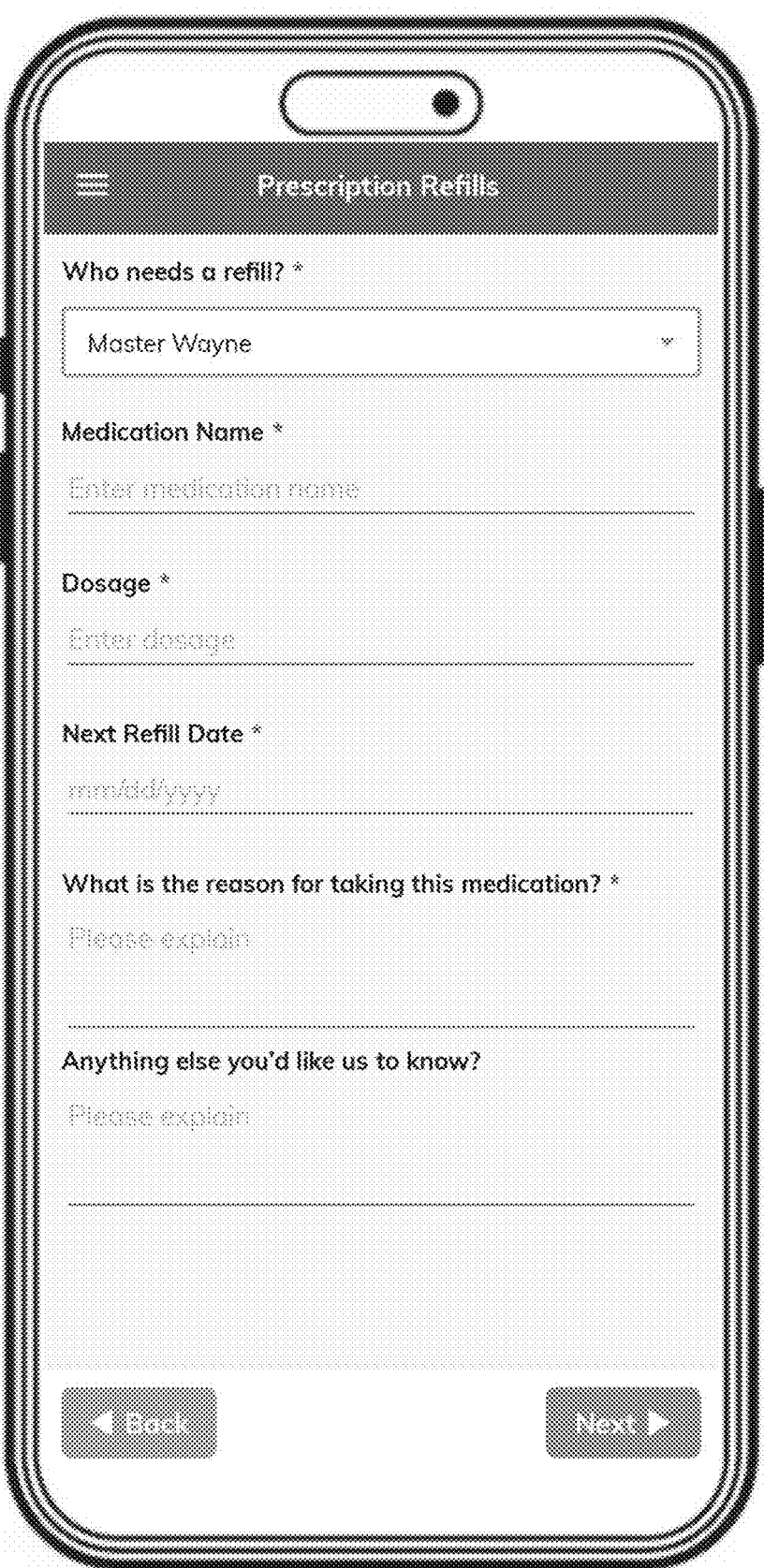
FIG. 9 is an exemplary GUI display of a platform of the present invention.

FIG. 9 depicts a prescription refill portal. The portal is operable to receive information relating to the member, medication, dosage, refill date, reason for taking the medication, and other information. In one embodiment, this information is submitted to a pharmacy. In one embodiment, this information is submitted to a medical professional. In one embodiment, a medical professional is operable to utilize the system of the present invention to authorize a refill request submitted by a patient user and transmit the refill request directly to a pharmacy.

Figure 10:
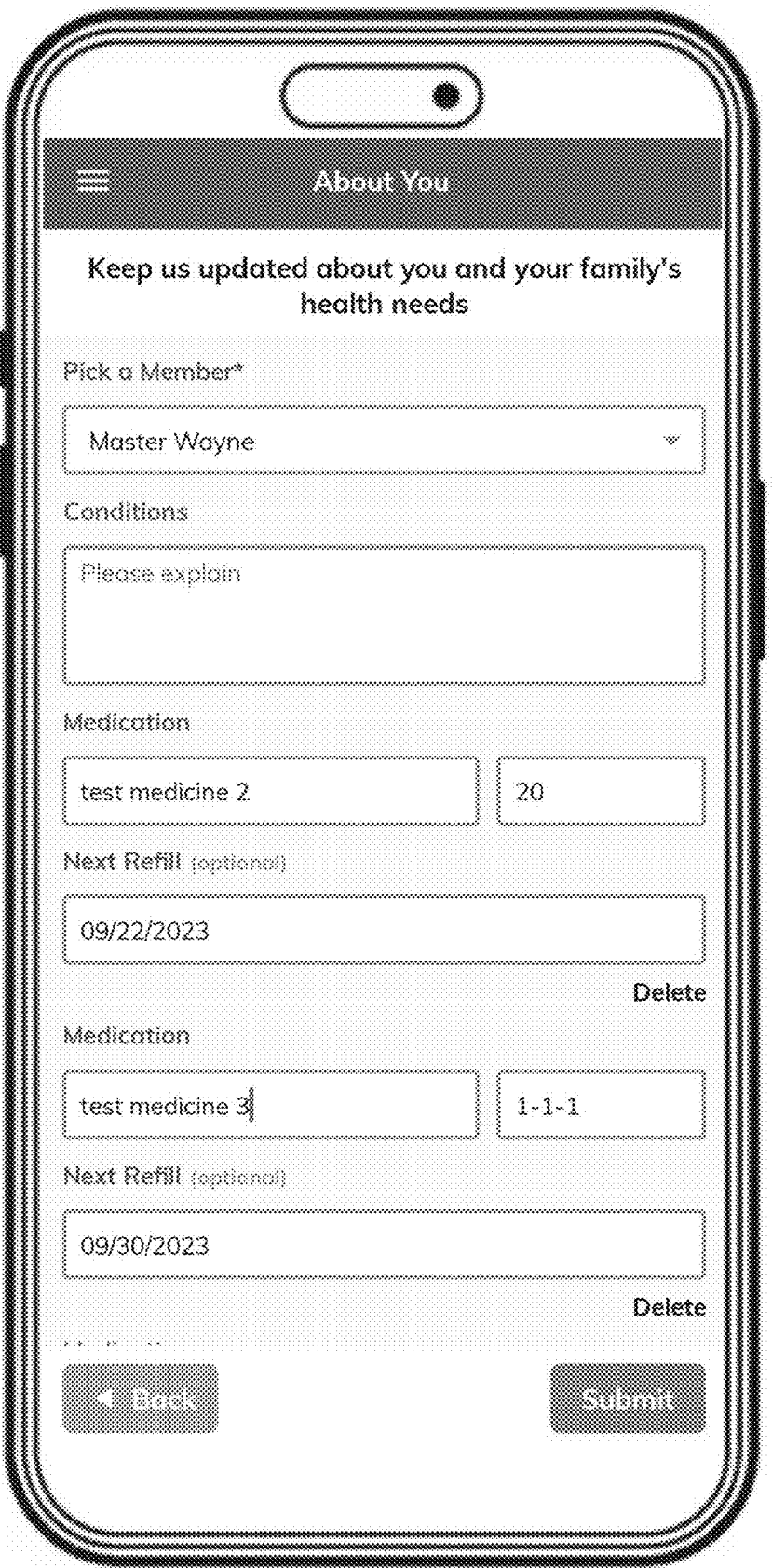
FIG. 10 is an exemplary GUI display of a platform of the present invention.
Figure 11:
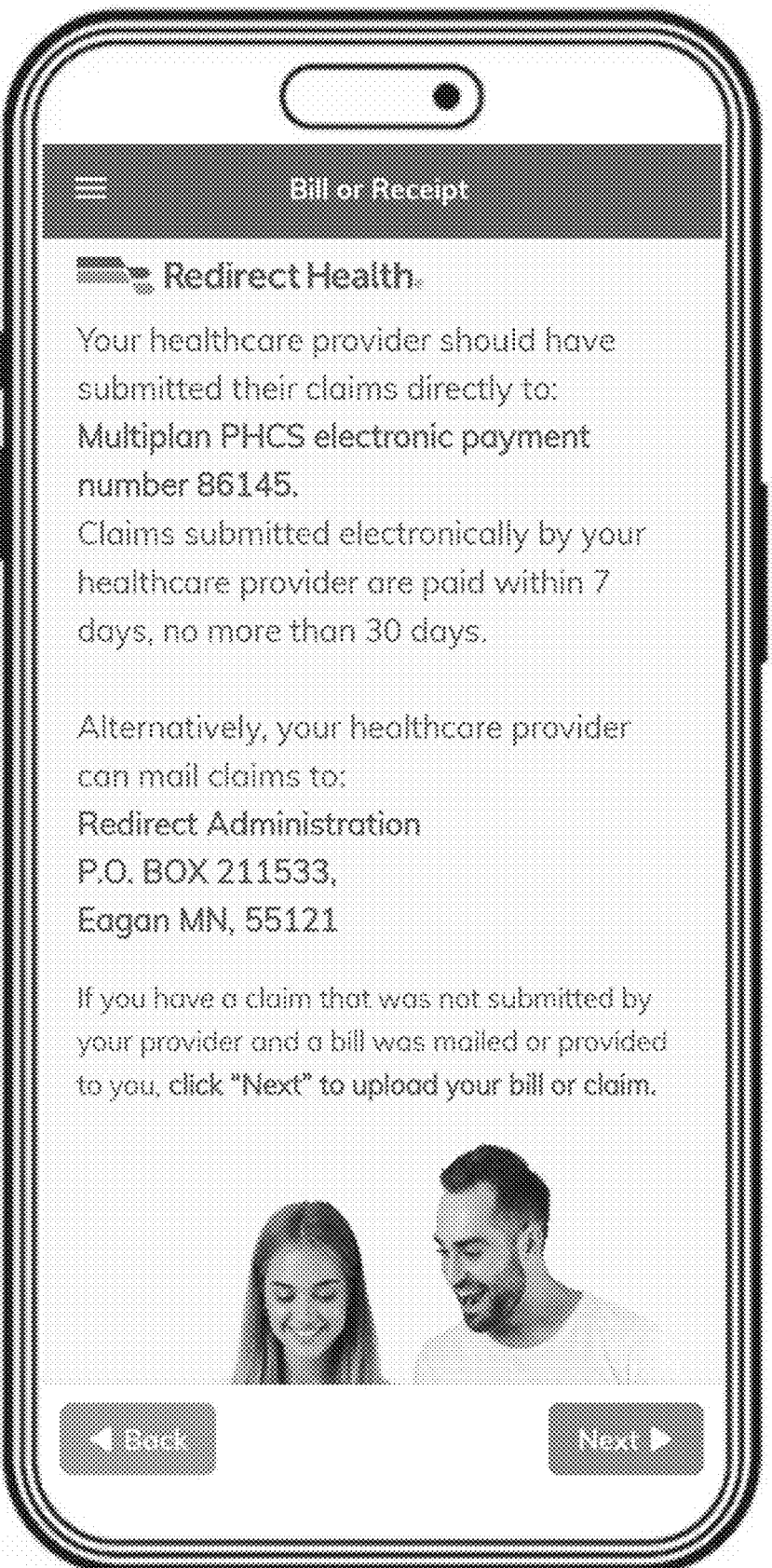
FIG. 11 is an exemplary GUI display of a platform of the present invention.
Figure 12:
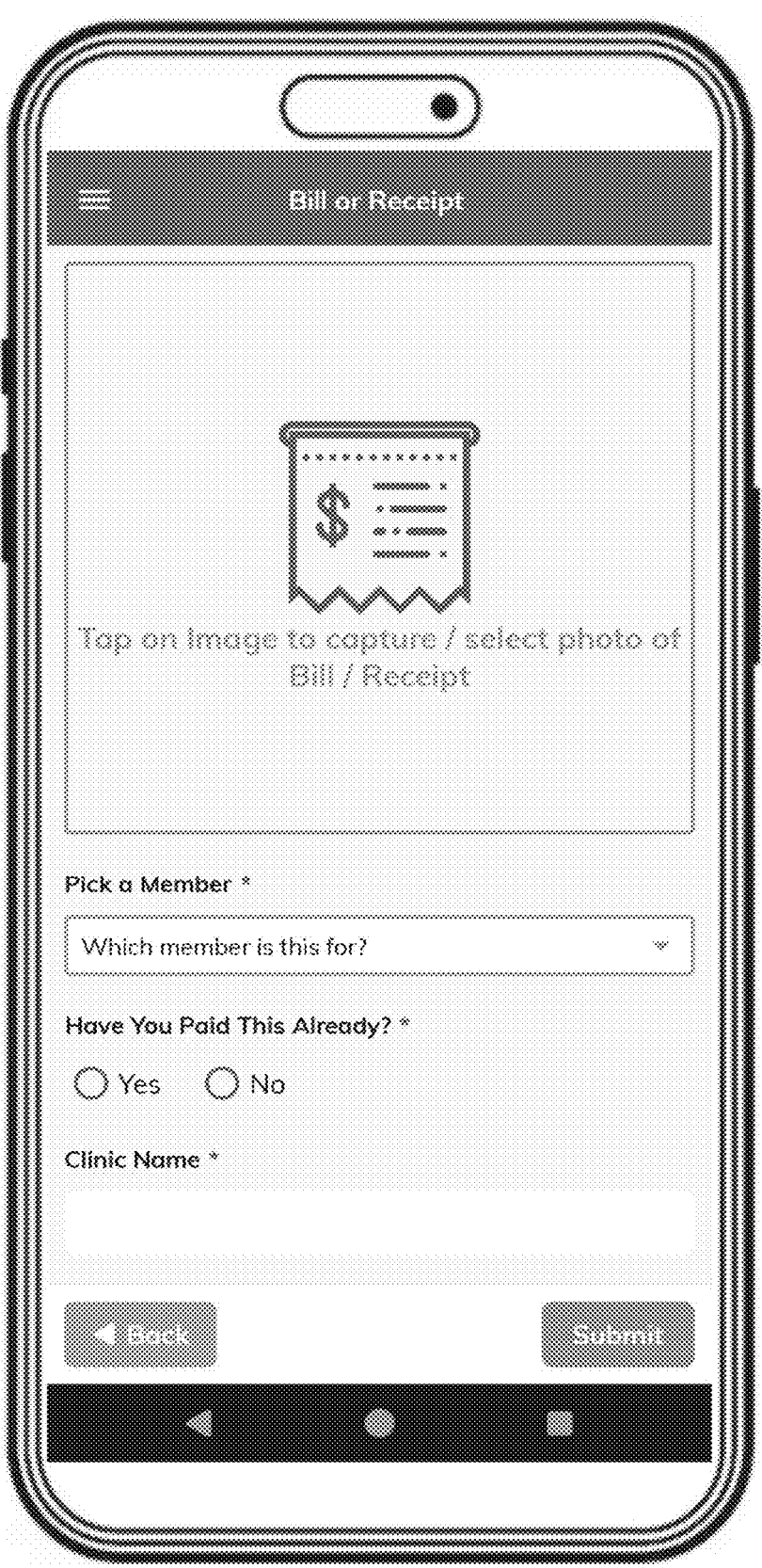
FIG. 12 is an exemplary GUI display of a platform of the present invention.

FIG. 10 depicts an exemplary medical record display for a user of the system of the present invention. The GUI is operable to receive user information relating to medical history including any existing conditions or diagnoses, medications, treatments, or other information. FIG. 11 depicts a billing information messaging portal which enables the system of the present invention to receive and provide billing information based on provided medical goods and services. The system is further configured to capture and convert a bill or receipt into a digital data set. An imaging system of a user device captures an image of the bill or receipt, and the NLP model of the present invention converts the information into a digital dataset for analysis and storage. A user is further operable to input additional information relating to the bill or receipt which will be incorporated into the digital data set.

Figure 13:
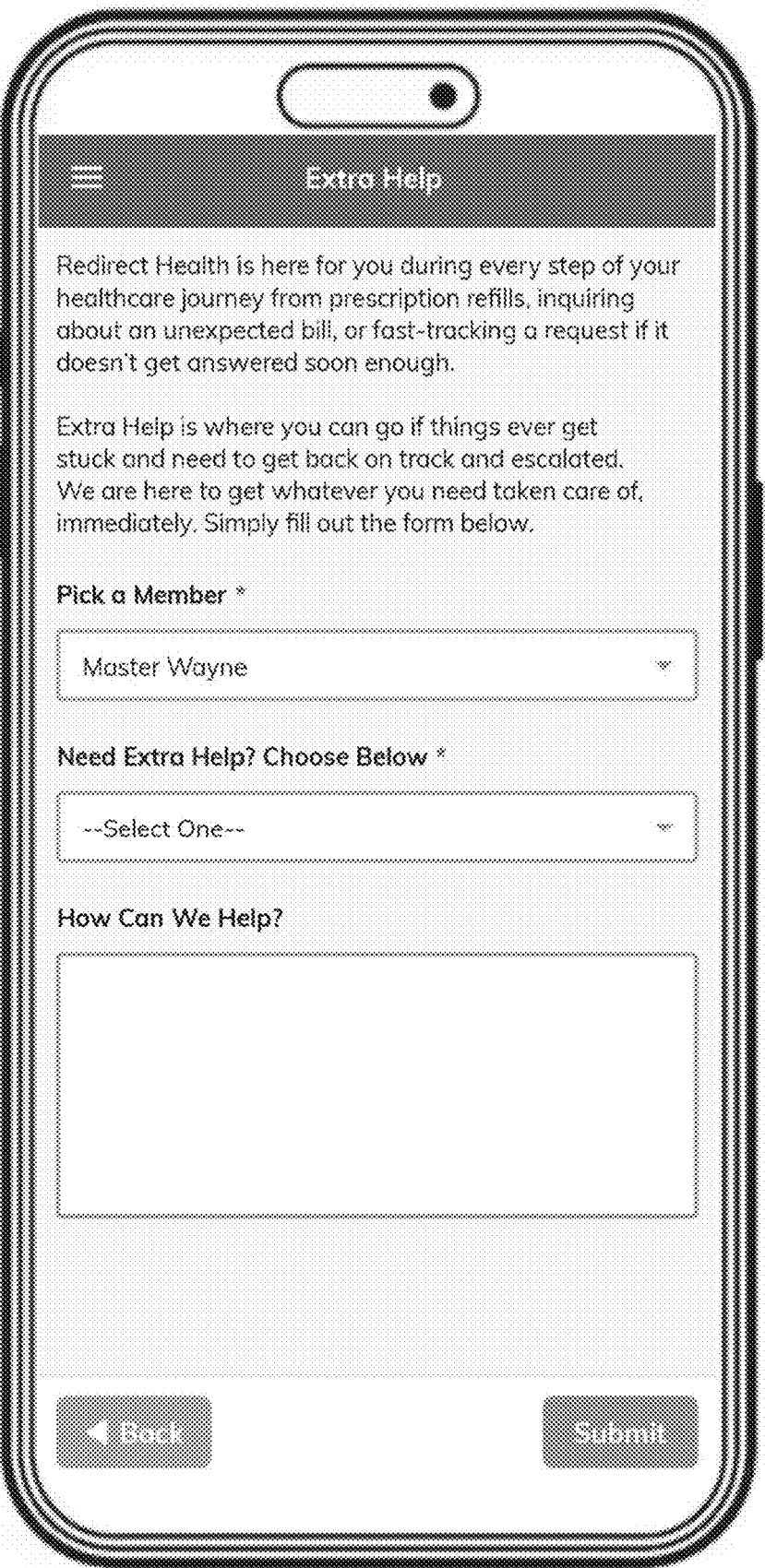
FIG. 13 is an exemplary GUI display of a platform of the present invention.

FIG. 13 illustrates a help portal through which a user is operable to communicate with the system of the present invention. In one embodiment, the system of the present invention implements an artificial intelligence chatbot for the communication of information and dynamic suggestion of solutions based on an input. In one embodiment, the help portal of the present invention connects a patient user with an administrative user for assistance in navigating and utilizing the system of the present invention.

Figure 14:
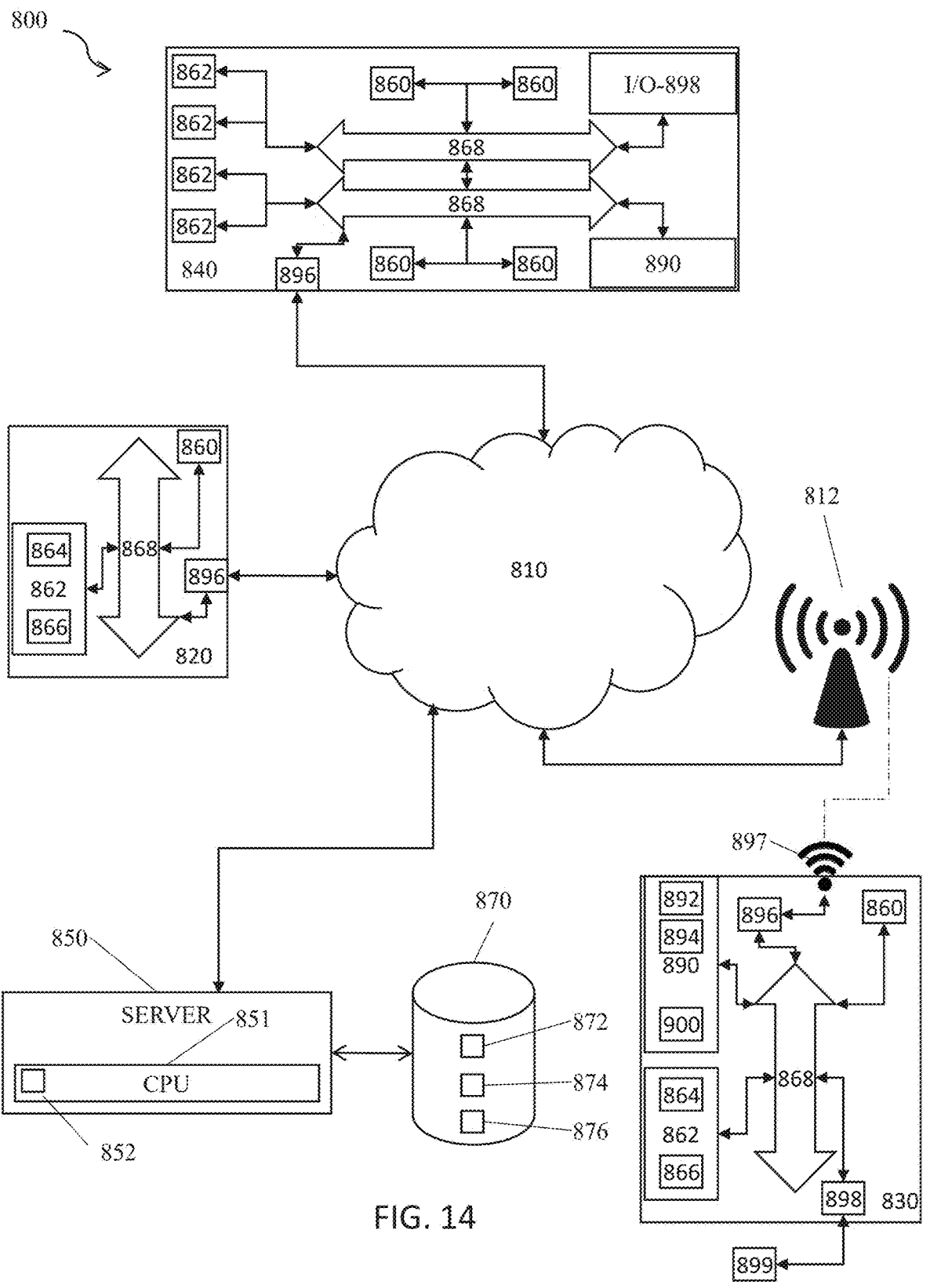
FIG. 14 is a schematic diagram of a system of the present invention.

FIG. 14 is a schematic diagram of an embodiment of the invention illustrating a computer system, generally described as 800, having a network 810, a plurality of computing devices 820, 830, 840, a server 850, and a database 870.

The server 850 is constructed, configured, and coupled to enable communication over a network 810 with a plurality of computing devices 820, 830, 840. The server 850 includes a processing unit 851 with an operating system 852. The operating system 852 enables the server 850 to communicate through network 810 with the remote, distributed user devices. Database 870 is operable to house an operating system 872, memory 874, and programs 876.

In one embodiment of the invention, the system 800 includes a network 810 for distributed communication via a wireless communication antenna 812 and processing by at least one mobile communication computing device 830. Alternatively, wireless and wired communication and connectivity between devices and components described herein include wireless network communication such as WI-FI, WORLDWIDE INTEROPERABILITY FOR MICROWAVE ACCESS (WIMAX), Radio Frequency (RF) communication including RF identification (RFID), NEAR FIELD COMMUNICATION (NFC), BLUETOOTH including BLUETOOTH LOW ENERGY (BLE), ZIGBEE, Infrared (IR) communication, cellular communication, satellite communication, Universal Serial Bus (USB), Ethernet communications, communication via fiber-optic cables, coaxial cables, twisted pair cables, and/or any other type of wireless or wired communication. In another embodiment of the invention, the system 800 is a virtualized computing system capable of executing any or all aspects of software and/or application components presented herein on the computing devices 820, 830, 840. In certain aspects, the computer system 800 is operable to be implemented using hardware or a combination of software and hardware, either in a dedicated computing device, or integrated into another entity, or distributed across multiple entities or computing devices.

By way of example, and not limitation, the computing devices 820, 830, 840 are intended to represent various forms of electronic devices including at least a processor and a memory, such as a server, blade server, mainframe, mobile phone, personal digital assistant (PDA), smartphone, desktop computer, netbook computer, tablet computer, workstation, laptop, and other similar computing devices. The components shown here, their connections and relationships, and their functions, are meant to be exemplary only, and are not meant to limit implementations of the invention described and/or claimed in the present application.

In one embodiment, the computing device 820 includes components such as a processor 860, a system memory 862 having a random access memory (RAM) 864 and a read-only memory (ROM) 866, and a system bus 868 that couples the memory 862 to the processor 860. In another embodiment, the computing device 830 is operable to additionally include components such as a storage device 890 for storing the operating system 892 and one or more application programs 894, a network interface unit 896, and/or an input/output controller 898. Each of the components is operable to be coupled to each other through at least one bus 868. The input/output controller 898 is operable to receive and process input from, or provide output to, a number of other devices 899, including, but not limited to, alphanumeric input devices, mice, electronic styluses, display units, touch screens, gaming controllers, joy sticks, touch pads, signal generation devices (e.g., speakers), augmented reality/virtual reality (AR/VR) devices (e.g., AR/VR headsets), or printers.

By way of example, and not limitation, the processor 860 is operable to be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that can perform calculations, process instructions for execution, and/or other manipulations of information.

In another implementation, shown as 840 in FIG. 14, multiple processors 860 and/or multiple buses 868 are operable to be used, as appropriate, along with multiple memories 862 of multiple types (e.g., a combination of a DSP and a microprocessor, a plurality of microprocessors, one or more microprocessors in conjunction with a DSP core).

Also, multiple computing devices are operable to be connected, with each device providing portions of the necessary operations (e.g., a server bank, a group of blade servers, or a multi-processor system). Alternatively, some steps or methods are operable to be performed by circuitry that is specific to a given function.

According to various embodiments, the computer system 800 is operable to operate in a networked environment using logical connections to local and/or remote computing devices 820, 830, 840 through a network 810. A computing device 830 is operable to connect to a network 810 through a network interface unit 896 connected to a bus 868. Computing devices are operable to communicate communication media through wired networks, direct-wired connections or wirelessly, such as acoustic, RF, or infrared, through an antenna 897 in communication with the network antenna 812 and the network interface unit 896, which are operable to include digital signal processing circuitry when necessary. The network interface unit 896 is operable to provide for communications under various modes or protocols.

In one or more exemplary aspects, the instructions are operable to be implemented in hardware, software, firmware, or any combinations thereof. A computer readable medium is operable to provide volatile or non-volatile storage for one or more sets of instructions, such as operating systems, data structures, program modules, applications, or other data embodying any one or more of the methodologies or functions described herein. The computer readable medium is operable to include the memory 862, the processor 860, and/or the storage media 890 and is operable be a single medium or multiple media (e.g., a centralized or distributed computer system) that store the one or more sets of instructions 900. Non-transitory computer readable media includes all computer readable media, with the sole exception being a transitory, propagating signal per se. The instructions 900 are further operable to be transmitted or received over the network 810 via the network interface unit 896 as communication media, which is operable to include a modulated data signal such as a carrier wave or other transport mechanism and includes any delivery media. The term "modulated data signal" means a signal that has one or more of its characteristics changed or set in a manner as to encode information in the signal.

Storage devices 890 and memory 862 include, but are not limited to, volatile and non-volatile media such as cache, RAM, ROM, EPROM, EEPROM, FLASH memory, or other solid state memory technology; discs (e.g., digital versatile discs (DVD), HD-DVD, BLU-RAY, compact disc (CD), or CD-ROM) or other optical storage; magnetic cassettes, magnetic tape, magnetic disk storage, floppy disks, or other magnetic storage devices; or any other medium that can be used to store the computer readable instructions and which can be accessed by the computer system 800.

In one embodiment, the computer system 800 is within a cloud-based network. In one embodiment, the server 850 is a designated physical server for distributed computing devices 820, 830, and 840. In one embodiment, the server 850 is a cloud-based server platform. In one embodiment, the cloud-based server platform hosts serverless functions for distributed computing devices 820, 830, and 840.

In another embodiment, the computer system 800 is within an edge computing network. The server 850 is an edge server, and the database 870 is an edge database. The edge server 850 and the edge database 870 are part of an edge computing platform. In one embodiment, the edge server 850 and the edge database 870 are designated to distributed computing devices 820, 830, and 840. In one embodiment, the edge server 850 and the edge database 870 are not designated for distributed computing devices 820, 830, and 840. The distributed computing devices 820, 830, and 840 connect to an edge server in the edge computing network based on proximity, availability, latency, bandwidth, and/or other factors.

It is also contemplated that the computer system 800 is operable to not include all of the components shown in FIG. 14, is operable to include other components that are not explicitly shown in FIG. 14, or is operable to utilize an architecture completely different than that shown in FIG. 14. The various illustrative logical blocks, modules, elements, circuits, and algorithms described in connection with the embodiments disclosed herein are operable to be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application (e.g., arranged in a different order or partitioned in a different way), but such implementation decisions should not be interpreted as causing a departure from the scope of the present invention.

Location data is created and used by the present invention using one or more hardware and/or software components. By way of example and not limitation, location data is created using the Global Positioning System (GPS), low energy BLUETOOTH based systems such as beacons, wireless networks such as WIFI, Radio Frequency (RF) including RF Identification (RFID), Near Field Communication (NFC), magnetic positioning, and/or cellular triangulation. By way of example, location data is determined via an Internet Protocol (IP) address of a device connected to a wireless network. A wireless router is also operable to determine identities of devices connected to the wireless network through the router, and thus is operable to determine the locations of these devices through their presence in the connection range of the wireless router.

Certain modifications and improvements will occur to those skilled in the art upon a reading of the foregoing description. The above-mentioned examples are provided to serve the purpose of clarifying the aspects of the invention and it will be apparent to one skilled in the art that they do not serve to limit the scope of the invention. All modifications and improvements have been deleted herein for the sake of conciseness and readability but are properly within the scope of the present invention.

The invention claimed is:

1. A system for dynamic healthcare navigation, comprising:

a server computer including a data warehouse, a memory, and a processor; and at least one database comprising at least one secure data set;

wherein the server computer further includes a platform for receiving additional information from a user device and transmitting the additional information to the server computer;

wherein the platform is operable to capture an image of a bill and/or receipt and convert the image of the bill and/or receipt into a digital data set using natural language processing (NLP);

wherein the at least one database is integrated with at least one automated call center system, operable to automatically collect audio data from one or more remote user devices;

wherein the at least one automated call center system includes at least one NLP module configured to automatically transcribe and semantically analyze the collected audio data;

wherein the server computer is configured to access the at least one secure data set and store the at least one secure data set in the data warehouse;

wherein the data warehouse implements a machine learning model (MLM), wherein the MLM is configured to analyze the at least one secure data set and tag predictors within the at least one secure data set;

wherein the server computer is configured to receive a request associated with the predictors within the at least one secure data set;

wherein the server computer is configured to generate a first output;

wherein the server computer is configured to receive a designation of a plurality of individuals and automatically aggregate components of the at least one secure data set concerned with the designated plurality of individuals;

wherein the server computer is configured to generate a second output based on predictors for the aggregated components of the at least one secure data set;

wherein the MLM includes at least one artificial neural network (ANN);

wherein the at least one ANN includes a plurality of node layers;

wherein the plurality of node layers includes an input layer, one or more hidden layers, and an output layer;

wherein each node of the plurality of node layers connects to another node of the plurality of node layers and includes an associated weight and threshold;

wherein an output of any one node of the plurality of node layers must exceed a specified threshold to be activated;

wherein activating any one node of the plurality of node
layers includes sending data to a next node layer of the
plurality of node layers; and wherein the at least one ANN produces the predictors.

2. The system of claim 1, wherein the additional infor-
mation comprises contact information, a request associated
with the predictors, or payment information from data.

3. The system of claim 1, further comprising at least one
authorization for the at least one secure data set, wherein the
at least one authorization is granted by a medical license, an
insurance license, or a third-party administrator (TPA)
license.

4. The system of claim 1, wherein the MLM is trained
using the first output, wherein the first output is converted
into a training input, wherein the training input is fed back
into the MLM.

5. The system of claim 1, wherein the predictors are
assigned a weight, wherein the weight is a numerical value,
wherein a larger weight predictor contributes more signifi-
cantly to an outcome than a smaller weight predictor.

6. The system of claim 1, wherein the first output includes
a healthcare treatment suggestion, a predicted likelihood of
success of a treatment plan, or an estimated claim payment.

7. The system of claim 1, wherein the system implements
at least one smart contract configured to automatically
implement at least one authorization, access to the at least
one secure data set, and store the at least one secure data set
in the data warehouse.

8. The system of claim 1, wherein the system is further
configured to generate a narrative summary of the at least
one secure data set, an outcome, or the predictors.

9. A system for dynamic healthcare navigation, compris-
ing:

a server computer including a data warehouse, a memory,
and a processor; and at least one database comprising
at least one secure data set;

wherein the server computer further includes a platform
for receiving additional information from a user device
and transmitting the additional information to the
server computer;

wherein the platform is operable to capture an image of a
bill and/or receipt and convert the image of the bill
and/or receipt into a digital data set using natural
language processing (NLP);

wherein the server computer is configured to access the at
least one secure data set and store the at least one secure
data set in the data warehouse;

wherein the data warehouse implements a machine learn-
ing model (MLM), wherein the MLM is configured to
analyze the at least one secure data set and tag predic-
tors within the at least one secure data set;

wherein the server computer is configured to receive a
request associated with the predictors within the at least
one secure data set;

wherein the server computer is configured to generate a
first output based on the predictors within the at least
one secure data set;

wherein the server computer is configured to receive a
designation of a plurality of individuals and automati-
cally aggregate components of the at least one secure
data set concerned with the designated plurality of
individuals;

wherein the server computer is configured to generate a
second output;

wherein the MLM includes at least one artificial neural
network (ANN);

wherein the at least one ANN includes a plurality of node
layers;

wherein the plurality of node layers includes an input
layer, one or more hidden layers, and an output layer;

wherein each node of the plurality of node layers connects
to another node of the plurality of node layers and
includes an associated weight and threshold;

wherein an output of any one node of the plurality of node
layers must exceed a specified threshold to be acti-
vated;

wherein activating any one node of the plurality of node
layers includes sending data to a next node layer of the
plurality of node layers; and wherein the at least one ANN produces the predictors.

10. The system of claim 9, wherein the first output
includes a healthcare treatment suggestion, a predicted like-
lihood of success of a treatment plan, or an estimated claim
payment.

11. The system of claim 9, wherein the MLM is trained
using the first output, wherein the first output is converted
into a training input, wherein the training input is fed back
into the MLM.

12. The system of claim 9, wherein the additional infor-
mation comprises contact information, the request associ-
ated with the predictors, or payment information from data.

13. The system of claim 9, wherein the system is further
configured to generate a narrative summary of the at least
one secure data set, an outcome, or the predictors.

14. A system for dynamic healthcare navigation, compris-
ing:

a server computer including a data warehouse, a memory,
and a processor; and at least one database comprising at least one secure data
set;

wherein the server computer further includes a platform
for receiving additional information from a user device
and transmit ting the additional information to the
server computer;

wherein the server computer is configured to access the at
least one secure data set and store the at least one secure
data set in the data warehouse;

wherein the data warehouse implements a machine learn-
ing model (MLM), wherein the MLM is configured to
analyze the at least one secure data set and tag predic-
tors within the at least one secure data set;

wherein the server computer is configured to receive a
request associated with the predictors within the at least
one secure data set;

wherein the server computer is configured to generate a
first output;

wherein the server computer is configured to receive a
designation of a plurality of individuals and automati-
cally aggregate components of the at least one secure
data set concerned with the designated plurality of
individuals;

wherein the server computer is configured to generate a
second output;

wherein the MLM includes at least one artificial neural
network (ANN);

wherein the at least one ANN includes a plurality of node
layers;

wherein the plurality of node layers include an input layer,
one or more hidden layers, and an output layer;

wherein each node of the plurality of node layers connects
to another node of the plurality of node layers and
includes an associated weight and threshold;

wherein an output of any one node of the plurality of node layers must exceed a specified threshold to be activated;

wherein activating any one node of the plurality of node layers includes sending data to a next node layer of the plurality of node layers; and wherein the at least one ANN produces the predictors.

15. The system of claim 14, wherein the additional information comprises contact information, the request associated with the predictors, or payment information from data.

16. The system of claim 14, further comprising at least one authorization for the at least one secure data, wherein the at least one authorization is granted by a medical license, an insurance license, or a third-party administrator (TPA) license.

17. The system of claim 14, wherein the MLM is trained using the first output, wherein the first output is converted into a training input, wherein the training input is fed back into the MLM.

18. The system of claim 14, wherein the predictors are assigned a weight, wherein the weight is a numerical value, wherein a larger weight predictor contributes more significantly to an outcome than a smaller weight predictor.

19. The system of claim 14, wherein the first output includes a healthcare treatment suggestion, a predicted likelihood of success of a treatment plan, or an estimated claim payment.

20. The system of claim 14, wherein the system implements at least one smart contract configured to automatically implement at least one authorization, access to the at least one secure data set, and store the at least one secure data set in the data warehouse.

*     *     *     *     *